US011118232B2

(12) United States Patent
Jones et al.

(10) Patent No.: US 11,118,232 B2
(45) Date of Patent: Sep. 14, 2021

(54) METHODS OF DETECTING DDR2 MUTATIONS

(71) Applicant: QUEST DIAGNOSTICS INVESTMENTS LLC, Secaucus, NJ (US)

(72) Inventors: Daniel M. Jones, Chantilly, VA (US); Yongbao Wang, Chantilly, VA (US); Shere Billouin-Frazier, Chantilly, VA (US); Justin Windham, Chantilly, VA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 197 days.

(21) Appl. No.: 16/221,944

(22) Filed: Dec. 17, 2018

(65) Prior Publication Data

US 2019/0177801 A1 Jun. 13, 2019

Related U.S. Application Data

(60) Continuation of application No. 15/455,509, filed on Mar. 10, 2017, now Pat. No. 10,155,994, which is a division of application No. 14/141,022, filed on Dec. 26, 2013, now Pat. No. 9,617,579.

(60) Provisional application No. 61/746,303, filed on Dec. 27, 2012, provisional application No. 61/874,660, filed on Sep. 6, 2013.

(51) Int. Cl.
| | |
|---|---|
| *C12Q 1/68* | (2018.01) |
| *A61K 31/437* | (2006.01) |
| *C07K 16/40* | (2006.01) |
| *C12Q 1/6886* | (2018.01) |
| *G01N 33/574* | (2006.01) |
| *A61K 31/506* | (2006.01) |
| *A61K 31/713* | (2006.01) |
| *A61P 35/00* | (2006.01) |
| *A61K 45/06* | (2006.01) |
| *C12Q 1/48* | (2006.01) |

(52) U.S. Cl.
CPC .......... *C12Q 1/6886* (2013.01); *A61K 31/437* (2013.01); *A61K 31/506* (2013.01); *A61K 31/713* (2013.01); *A61K 45/06* (2013.01); *A61P 35/00* (2018.01); *C07K 16/40* (2013.01); *C12Q 1/485* (2013.01); *C12Q 1/68* (2013.01); *C12Y 207/10001* (2013.01); *C12Y 207/11001* (2013.01); *G01N 33/5743* (2013.01); *C12Q 2600/156* (2013.01); *C12Q 2600/16* (2013.01); *G01N 2333/912* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 9,617,579 B2 * | 4/2017 | Jones | A61K 45/06 |
| 10,155,994 B2 * | 12/2018 | Jones | A61K 45/06 |
| 2003/0050470 A1 * | 3/2003 | An | C07K 14/82 536/24.3 |
| 2010/0068207 A1 * | 3/2010 | Fanidi | G01N 33/57484 514/1.1 |
| 2011/0009288 A1 | 1/2011 | Talantov et al. | |
| 2011/0159608 A1 * | 6/2011 | Graham | A61P 27/02 436/501 |
| 2011/0287011 A1 | 11/2011 | Gurney et al. | |
| 2012/0295819 A1 * | 11/2012 | Leamon | C12Q 1/6806 506/26 |
| 2013/0005613 A1 * | 1/2013 | Leamon | C12Q 1/6886 506/26 |
| 2013/0011881 A1 * | 1/2013 | Leamon | C12Q 1/6806 435/91.2 |
| 2013/0059738 A1 * | 3/2013 | Leamon | C12Q 1/6855 506/2 |
| 2013/0059762 A1 * | 3/2013 | Leamon | C12Q 1/6806 506/26 |

FOREIGN PATENT DOCUMENTS

| | | |
|---|---|---|
| WO | WO 2006/110587 A2 | 10/2006 |
| WO | WO 2011/019704 A2 | 2/2011 |
| WO | WO 2011/050120 A1 | 4/2011 |

OTHER PUBLICATIONS

Genbank Accession No. NM_006182—*Homo sapiens* discoidin domain receptor tyrosine kinase 2 (DDR2), transcript variant 2, mRNA (first deposited on Mar. 2, 2005, retrieved on Dec. 18, 2020 from http://www.ncbi.nlm.nih.gov/nuccore/NM_006182). (Year: 2005).*
Genbank Accession No. NM_004333—*Homo sapiens* B-Raf proto-oncogene, serine/threonine kinase (BRAF), transcript variant 1, mRNA (first deposited Apr. 7, 2003, retrieved on Dec. 18, 2020 from http://www.ncbi.nlm.nih.gov/nuccore/NM_004333). (Year: 2003).*
Genbank Accession No. NG_007873—*Homo sapiens* B-Raf proto-oncogene, serine/threonine kinase (BRAF), RefSeqGene (LRG_299) on chromosome 7 (first deposited Mar. 4, 2012, retrieved on Dec. 18, 2020 from http://www.ncbi.nlm.nih.gov/nuccore/NG_007873). (Year: 2012).*

(Continued)

*Primary Examiner* — Teresa E Strzelecka
*Assistant Examiner* — Olayinka A Oyeyemi
(74) *Attorney, Agent, or Firm* — Foley & Lardner LLP

(57) ABSTRACT

Described herein are methods for diagnosing melanoma or basal cell carcinoma based on mutations in the DDR2 gene. Further, a distinct subgroup of BRAF-mutated melanomas have somatic mutations in the DDR2 gene as well. Applications of this finding to routine diagnostics include the molecular stratification of melanoma, and the tissue identification of targetable DDR2 kinase mutations in routine formalin-fixed paraffin-embedded sections. Described herein are methods, compositions and kits related to the discovery that DDR2 mutations may be markers for melanoma generally, and BRAF-mediated melanoma in particular, opening up the possibility of dual therapy for melanoma by targeting both DDR2 and BRAF.

7 Claims, 6 Drawing Sheets

Specification includes a Sequence Listing.

(56) References Cited

OTHER PUBLICATIONS

SantaLucia Jr, John. Physical principles and visual-OMP software for optimal PCR design. PCR Primer Design. Humana Press, 2007: pp. 3-33. (Year: 2007).*

Saldanha G, Purnell D, Fletcher A, Potter L, Gillies A, Pringle JH. High BRAF mutation frequency does not characterize all melanocytic tumor types. International journal of cancer. Sep. 20, 2004; 111(5)705-10. (Year: 2004).*

Urbankova et al., 2012. Recurrent breakpoints in 14q32. 13/TCL1A region in mature B-cell neoplasms with villous lymphocytes. Leukemia & Lymphoma, 53(12), pp. 2449-2455. (Year: 2012).*

Ahr, A., Holtrich, U., Solbach, C., Scharl, A., Strebhardt, K., Karn, T. and Kaufmann, M., 2001. Molecular classification of breast cancer patients by gene expression profiling. The Journal of Pathology: A Journal of the Pathological Society of Great Britain and Ireland, 195(3), pp. 312-320. (Year: 2001).*

Ricordel et al., 2018. Mutational landscape of DDR2 gene in lung squamous cell carcinoma using next-generation sequencing. Clinical lung cancer, 19(2), pp. 163-169. (Year: 2018).*

Sasaki, H., Shitara, M., Yokota, K., Okuda, K., Hikosaka, Y., Moriyama, S., Yano, M. and Fujii, Y., 2012. DDR2 polymorphisms and mRNA expression in lung cancers of Japanese patients. Oncology letters, 4(1), pp. 33-37. (Year: 2012).*

Chapman, et al. "Improved Survival with Vemurafenib in Melanoma with BRAF V600E Mutation", The New England Journal of Medicine, Jun. 30, 2011, pp. 2507-2516.

Flaherty, et al. "Inhibition of Mutated, Activated BRAF in Metastatic Melanoma", Aug. 26, 2010, vol. 363, No. 9, pp. 809-819.

Hammerman, et al. "Mutations in the DDR2 Kinase Gene Identify a Novel Therapeutic Target in Squamous Cell Lung Cancer", Jun. 2011, Cancer Discovery, pp. 79-89.

Ruiz-Tachiquin, et al. "Molecular analysis of hepatitis B virus "A" determinant in asymptomatic and symptomatic Mexican carriers", Virology Journal, 2007, vol. 4, No. 6, pp. 1-7.

Vitart, et al. "SLC2A9 is a newly identified urate transporter influencing serum urate concentration, urate excretion and gout", Nature Genetics, Apr. 2008, vol. 40, No. 4, pp. 437-442.

Written Opinion & International Search Report in PCT/US2013/077832 dated Jun. 2, 2014.

Kelleher et al., "Molecular Therapeutic Advances in Personalized Therapy of Melanoma and Non-Small Cell Lung Cancer," Journal of Personalized Medicine, vol. 2, No. 4, pp. 35-49, Apr. 2012.

Valithan et al., "Discoidin domain receptor tyrosine kinases: new players in cancer progression," Cancer and Metastasis Reviews, vol. 31, No. 1-2, Feb. 2012.

Supplementary European Search Report dated Jul. 8, 2016 in application No. EP 13866601.

Office Action dated Jul. 6, 2015 in U.S. Appl. No. 14/141,022.
Office Action dated Oct. 22, 2015 in U.S. Appl. No. 14/141,022.
Office Action dated May 19, 2016 in U.S. Appl. No. 14/141,022.
Notice of Allowance dated Dec. 2, 2016 in U.S. Appl. No. 14/141,022.
Office Action dated Mar. 19, 2018 in U.S. Appl. No. 15/455,509.
Notice of Allowance dated Aug. 8, 2018 in U.S. Appl. No. 15/455,509.

* cited by examiner

FIG. 1A

DDR2 alignment (top lines) with DDR1 (bottom) showing conserved sequence between the two proteins at the sites of DDR2 mutations seen in extracellular-TM domains (amino acids 22-200) and the kinase domain (amino acids 550 to 851)

```
Query   22    KAQVNPAICRYPLGMSGGQIPDEDITASSQWSESTAAKYGRLDSEEGDGAWCPEIPVEPD   81
              K   +PA CRY LGM     IPD DI+ASS WS+STAA++ RL+S +GDGAWCP   V P
Sbjct   23    KGHFDPAKCRYALGMQDRTIPDSDISASSSWSDSTAARHSRLESSDGDGAWCPAGSVFPK   82
                                        R105C
Query   82    DLKEFLQIDLHTLHFITLVGTQGRHAGGHGIEFAPMYKINYSRDGTRWISWRNRHGKQVL   141
              + +E+LQ+DL  LH + LVGTQGRHAGG G EF+  Y++ YSRDG RW+ W++R G++V+
Sbjct   83    E-EEYLQVDLQRLHLVALVGTQGRHAGGLGKEFSRSYRLRYSRDGRRWMGWKDRWGQEVI   141

Query   142   DGNSNPYDIFLKDLEPPIVARFVRFIPVTDHSMNVCMRVELYGCVWLDGLVSYNAPAGQQ   201
                GN +P  + LKDL PP+VAR VRF P   D  M+VC+RVELYGC+W DGL+SY AP GQ
Sbjct   142   SGNEDPEGVVLKDLGPPMVARLVRFYPRADRVMSVCLRVELYGCLWRDGLLSYTAPVGQT   201

Query   202   FVLPGGSIIYLNDSVYDG-AVGYSMTEGLGQLTDGVSGLDDFTQTHEYHVWPGYDYVGWR   260
                 L    +YLNDS YDG  VG     GLGQL DGV GLDDF ++  E  VWPGYDYVGW
Sbjct   202   MYL--SEAVYLNDSTYDGHTVGGLQYGGLGQLADGVVGLDDFRKSQELRVWPGYDYVGWS   259

Query   261   NESATNGYIEIMFEFDRIRNFTTMKVHCNNMFAKGVKIFKEVQCYFR-SEASEWEPNAIS   319
              N S ++GY+E+ FEFDR+R F  M+VHCNNM   G ++   V+C FR   A  WE   +
Sbjct   260   NHSFSSGYVEMEFEFDRLRAFQAMQVHCNNMHTLGARLPGGVECRFRRGPAMAWEGEPMR   319

Query   320   FPLVLDDVNPSARFVTVPLHHRMASAIKCQYHFADTWMMFSEITFQSDAAMYNNSEALPT   379
                L  +  +P AR V+VPL  R+A  ++C++ FA  W++FSEI+F SD   + N+S AL
Sbjct   320   HNLGGNLGDPRARAVSVPLGGRVARFLQCRFLFAGPWLLFSEISFISDV-VNNSSPALGG   378

Query   380   S------------------PMAPTTYDPMLKVDDSNTRILIGCLVAIIFILLAIIVIIL   420
              +                    + P      P+ K + S T ILIGCLVAII +LL II ++L
Sbjct   379   TFPPAPWWPPGPPPTNFSSLELEPRGQQPVAKAEGSPTAILIGCLVAIILLLLIIALML   438

Query   421   WRQFWQKMLEKASRRMLDDEMTVSLSLPSDSSMFNNNRSSSPSEQGSNSTYDRIFPLRPD   480
              WR  W+++L  A RR+L++E+TV LS+P D+ + NN     P E              P
Sbjct   439   WRLHWRRLL-SAERRVLEEELTVHLSVPGDTILINNR--PGPREP-------------PP   482
                        I488S
Query   481   YQEPSRLIRKLPEFAP----GEEESGCSGVVKPVQPSGP-------EGVPHYAEADIVNL   529
              YQEP R    P  AP     G   SG   ++P +P  P            VPHYAEADIV L
Sbjct   483   YQEP-RPRGNPPHSAPCVPNGSAYSG--DYMEPEKPGAPLLPPPPQNSVPHYAEADIVTL   539
                                                F574C
Query   530   QGVTGGNTYSVPAVTMDLLSGKDVAVEEFPRKLLTFKEKLGEGQFGEVHLCEVEGMEKFK   589
              QGVTGGNTY+VPA+     + G     +FPR L FKEKLGEGQFGEVHLCEV+   +
Sbjct   540   QGVTGGNTYAVPALPPGAV-GDPPRVDFPRSRLRFKEKLGEGQFGEVHLCEVDSPQDLV   598

Query   590   DKDFALDVSANQPVLVAVKMLRADANKNARNDFLKEIKIMSRLKDPNIIHLLSVCITDDP   649
                DF L+V    P+LVAVK+LR DA KNARNDFLKE+KIMSRLKDPNII LL VC+ DDP
Sbjct   599   SLDFPLNVRKGHPLLVAVKILRPDATKNARNDFLKEVKIMSRLKDPNIIRLLGVCVQDDP   658
                                S667F
Query   650   LCMITEYMENGDLNQFLSRHE---------PPNSSSSDVRTVSYTNLKFMATQIASGMKY   700
              LCMIT+YMENGDLNQFLS H+         P +  ++     T+SY  L  +A QIASGM+Y
Sbjct   659   LCMITDYMENGDLNQFLSAHQLEDKAAEGAPGDGQAAQGPTISYPMLLHVAAQIASGMRY   718
                         L701F
Query   701   LSSLNFVHRDLATRNCLVGKNYTIKIADFGMSRNLYSGDYYRIQGRAVLPIRWMSWESIL   760
              L++LNFVHRDLATRNCLVG+N+TIKIADFGMSRNLY+GDYYR+QGRAVLPIRWM+WE IL
```

FIG. 1B

```
Sbjct   719   LATLNFVHRDLATRNCLVGENFTIKIADFGMSRNLYAGDYYRVQGRAVLPIRWMAWECIL   778

Query   761   LGKFTTASDVWAFGVTLWETFTFCQEQPYSQLSDEQVIENTGEFFRDQGRQTYLPQPAIC   820
              +GKFTTASDVWAFGVTLWE    C+ QP+ QL+DEQVIEN GEFFRDQGRQ YL +P  C
Sbjct   779   MGKFTTASDVWAFGVTLWEVLMLCRAQPFGQLTDEQVIENAGEFFRDQGRQVYLSRPPAC   838

Query   821   PDSVYKLMLSCWRRDTKNRPSFQEIHLLLLQ   851
              P  +Y+LML CW R+++ RP F ++H  L +
Sbjct   839   PQGLYELMLRCWSRESEQRPPFSQLHRFLAE   869
```

METHODS OF DETECTING DDR2 MUTATIONS

CROSS-REFERENCE TO RELATED APPLICATIONS

This application is a Continuation of U.S. application Ser. No. 15/455,509, filed Mar. 10, 2017, which is a Divisional of U.S. application Ser. No. 14/141,022, filed Dec. 26, 2013, which claims priority to U.S. Provisional Application Nos. 61/746,303, filed Dec. 27, 2012, and 61/874,660, filed Sep. 6, 2013.

The instant application contains a Sequence Listing which has been submitted in ASCII format via EFS-WEB and is hereby incorporated by reference in its entirety. Said ASCII copy, created on Dec. 13, 2018, is named sequence.txt and is 65 KB.

TECHNICAL FIELD

The present technology relates to novel mutations in the DDR2 gene in melanoma and basal cell carcinoma.

BACKGROUND

The following description is provided to assist the understanding of the reader. None of the information provided or references cited is admitted to be prior art to the present invention.

Melanoma and Basal Cell Carcinoma

Skin cancer is the most common of all cancers, afflicting more than one million Americans each year, a number that is rising rapidly. It is also the easiest to cure, if diagnosed and treated early. If allowed to progress to the point where it spreads to other sites, the prognosis is very poor. More than 8,000 melanoma deaths now occur per year.

Melanoma is a malignant tumor of melanocytes. Melanocytes predominantly occur in skin, between the outer layer of the skin (the epidermis) and the next layer (the dermis), but are also found in other parts of the body, including the bowel and the eye (see uveal melanoma). Melanoma can occur in any part of the body that contains melanocytes or as a metastatic tumor of unknown primary lesion. Melanoma is less common than other skin cancers but is much more dangerous and causes the majority (75%) of deaths related to skin cancer.

Melanoma arises from DNA damage to melanocytes. The early stage of the disease commonly begins with a radial growth phase when the tumor is confined to the epidermis followed by a dermal "vertical growth phase" (VGP). Some melanomas attain further invasive potential, growing into the surrounding tissue and may spread around the body through blood or lymph vessels to form metastases.

An immunological reaction against the tumor during the VGP may be judged by the presence and activity of the tumor infiltrating lymphocytes (TILs). These cells sometimes attack the primary tumor, and in certain cases, the primary tumor regresses with diagnosis of only the metastatic tumor.

Multiple genetic events have been related to the pathogenesis (disease development) of melanoma. Some cases of melanoma have a clear genetic predisposition. Germline mutations in CDKN2A, CDK4, MC1R, MDM2 SNP309 and in genes associated with xeroderma pigmentosum (XP) predispose patients to developing melanoma. Other cases of familial melanoma are genetically heterogeneous, and putative loci for familial melanoma have been identified on the chromosome arms 1p, 9p and 12q.

Clinical and Pathological diagnosis

Melanoma is usually first detected by visual examination of pigmented lesions of the skin, notably those that show: (A) asymmetry, (B) a border that is uneven, ragged, or notched, (C) coloring of different shades of brown, black, or tan and (D) diameter that has recently changed in size. In contrast, non-neoplastic moles or nevi are symmetrical, have a regular border, even coloration, and show no change in size/diameter over time. The main diagnostic concern is in distinguishing between a benign nevus, a dysplastic nevus-which may show progression over time, and a melanoma. Moles that are irregular in color or shape undergo further workup for melanoma. Following a visual examination and a dermatoscopic exam, or in vivo diagnostic tools such as a confocal microscope, a sample (biopsy) of the suspicious mole is usually obtained.

Sample Preparation

When an atypical mole has been identified, a skin biopsy takes place in order to best diagnose it. Local anesthetic is used to numb the area, then the mole is biopsied. The biopsy material is then sent to a laboratory to be evaluated by a pathologist. A skin biopsy can be a punch or shave biopsy, or complete excision. The complete excision is the preferred method, but a punch biopsy can suffice if the patient has cosmetic concerns (i.e. the patient does not want a scar) and the lesion is small. A scoop or deep shave biopsy is generally avoided due to risk of transecting a melanoma and thereby losing important prognostic information.

Most dermatologists and dermatopathologists use a diagnostic schema for classifying melanocytic lesions based on how symmetrical the lesion is and the degree of cytologic atypia in the melanocytes. In this classification, a nevus is classified as unequivocally benign, atypical/dysplastic, or clearly melanoma. A benign nevus exhibits no significant cytologic atypia and symmetrical growth. An atypical mole is read as having either asymmetrical growth, and/or having (mild, moderate, or severe) cytologic atypia. Usually, cytologic atypia is of more important clinical concern than architectural atypia. Along with melanoma, nevi with moderate to severe cytologic atypia may require further excision to make sure that the surgical margin is completely clear of the lesion.

Important aspects of the skin biopsy report for melanoma, including the pattern (presence/absence of an in situ component, radial or vertical growth), depth of invasion, presence of lymphocyte infiltrate, presence/absence of vascular or lymphatic invasion, presence/absence of a preexisting benign melanoma and the mitotic index. A further important aspect of the skin biopsy report for atypical nevi and melanoma is for the pathologist to indicate if the excision margin is clear of tumor. If there is any atypical melanocytes at the margin or if a melanoma is diagnosed, a reexcision is performed. Lymph node dissection may also be performed based on the tumor parameters seen on the initial biopsy and on the reexcision.

Further molecular testing may be performed on melanoma biopsies, reexcision or lymph node metastatic samples to assess for targetable genetic changes to help select optimal therapy.

BRAF

BRAF is a human gene that makes a protein called B-Raf. The gene is also referred to as proto-oncogene B-Raf and v-Raf murine sarcoma viral oncogene homolog B1, while the protein is more formally known as serine/threonine-protein kinase B-Raf. B-Raf is a member of the Raf kinase family of serine/threonine-specific protein kinases. This protein plays a role in regulating the MAP kinase/ERK signaling pathway, which affects cell division, differentiation, and growth factor expression.

In 2002, BRAF was shown to be mutated in human cancers. More than 30 mutations of the BRAF gene associated with human cancers have been identified. The frequency of BRAF mutations varies widely in human cancers from approximately 60% of melanomas and some types of benign nevi, to approximately 1-10% of common carcinomas such as lung adenocarcinoma (ACA) and colorectal cancer. In 90% of BRAF-mutated tumors, thymine is substituted for adenine at nucleotide 1799. This leads to valine (V) being substituted for by glutamate (E) at codon 600 (V600E) in the activation segment. This mutation has been widely observed in papillary thyroid carcinoma, colorectal cancer, melanoma and non-small-cell lung cancer. In June 2011, a team of Italian scientists used massively parallel sequencing to pinpoint mutation V600E as a likely driver mutation in 100% of cases of hairy cell leukemia. Less commonly, V600E mutation can also occur by a double nucleotide substitution.

BRAF mutations which have been found are R462I, I463S, G464E, G464V, G466A, G466E, G466V, G469A, G469E, N581S, E586K, D594V, F595L, G596R, L597V, T599I, V600D, V600E, V600K, V600R, K601E, E602K and A728V, etc. Most of these mutations are clustered in two regions of the gene: the glycine-rich P loop of the N lobe and the activation segment and flanking regions. Many of these mutations change the activation segment from an inactive state to an active state. For example in V600 mutations, the aliphatic side chain of Val600 interacts with the phenyl ring of Phe467 in the P loop. Replacing the medium-sized hydrophobic Val side chain with a larger and charged residue (such as the Val to Glu, Asp, Lys, or Arg changes seen in human tumors) can destabilize the interactions that maintain the DFG motif in an inactive conformation, resulting in conformational shift in the active position. Each BRAF kinase mutation has a variable effect on MEK phosphorylation activity, with most mutations having higher phosphorylation activity than the unmutated B-Raf protein, but some mutations show reduced or even absent kinase activity, termed "inhibitory" BRAF mutations. The effect of these inhibitory mutations appears to be to activate wild-type C-Raf, which then signals to ERK.

BRAF has also emerged as important drug target for tumor therapy. Drugs that treat cancers driven by BRAF mutations have been developed. On Aug. 17, 2011, one of them, vemurafenib, was approved by FDA for treatment of advanced-stage melanoma. Other BRAF-directed kinase inhibitors include GDC-0879, PLX-4720, sorafenib tosylate, dabrafenib, and LGX818.

DDR2

Discoidin domain receptor family, member 2, also known as DDR2 or CD167b (cluster of differentiation 167b), is a receptor tyrosine kinase (RTK) that regulates cell growth, differentiation, and metabolism in response to extracellular signals. DDR2 mutation has been previously reported in 3-4% of squamous cell carcinoma (SCC) of the lung. In lung SCC, a few cases with DDR2 mutation were shown to have clinical response to treatment with the tyrosine kinase inhibitor dasatinib (Cancer Discov. 2011 Apr. 3; 1(1): 78-89). The data suggested that DDR2 may be an important therapeutic target in SCC.

DDR2 protein comprises an extracellular discoidin (DS) domain, a transmembrane domain and a kinase domain. The kinase domain is located at amino acids 563 to 849 of the full length protein (which includes the signal peptide) and the DS domain is located at amino acids 22-399. The nucleotide sequence of human DDR2 mRNA variant 2 is shown in GenBank Accession no. NM_006182.

SUMMARY OF THE INVENTION

Methods of diagnosing melanoma in an individual are disclosed. In one aspect of the present invention, a method of diagnosing melanoma in an individual comprises
 (a) analyzing a biological sample from the individual,
 (b) detecting the presence of a nucleic acid encoding a DDR2 protein having a mutation selected from the group consisting of R105C, P321L, R458H, S467F, P476S, I488S, F574C, S667F, S674F, R680L, L701F, R742Q, and T836A in the sample, and
 (c) diagnosing the individual as having melanoma when the mutation is detected, thereby indicating that the individual has melanoma.

In another aspect, a method of diagnosing melanoma in an individual, comprises
 (a) analyzing a biological sample from the individual,
 (b) detecting the presence of a DDR2 protein having a mutation selected from the group consisting of R105C, P321L, R458H, S467F, P476S, I488S, F574C, S667F, S674F, R680L, L701F, R742Q, and T836A in the sample, and
 (c) diagnosing the individual as having melanoma when the mutation is detected, thereby indicating that the individual has melanoma.

In particular embodiments, the melanoma is advanced stage melanoma. The individual may have a skin lesion and/or may be suspected of having a skin disorder such as, for example, skin cancer, or melamona.

Methods of diagnosing basal cell carcinoma in an individual are also disclosed. In one aspect of the invention, a method of diagnosing basal cell carcinoma in an individual comprises
 (a) analyzing a biological sample from the individual,
 (b) detecting the presence of a nucleic acid encoding a DDR2 protein having a mutation selected from the group consisting of N146K, R399Q, and S702F in the sample, and
 (c) diagnosing the individual as having basal cell carcinoma when the mutation is detected, thereby indicating that the individual has basal cell carcinoma.

In another aspect of the invention, a method of diagnosing basal cell carcinoma in an individual, comprising
 (a) analyzing a biological sample from the individual,
 (b) detecting the presence of a DDR2 protein having a mutation selected from the group consisting N146K, R399Q, and S702F in the sample, and
 (c) diagnosing the individual as having basal cell carcinoma when the mutation is detected, thereby indicating that the individual has basal cell carcinoma.

The individual may have a skin lesion and/or may be suspected of having a skin disorder such as, for example, skin cancer, or basal cell carcinoma.

Also disclosed are methods for determining likelihood that an individual with melanoma or basal cell carcinoma will respond to treatment with a kinase inhibitor, comprising
 (a) analyzing a biological sample from the individual,
 (b) detecting the presence of a DDR2 mutation that confers sensitivity to a kinase inhibitor in a DDR2 protein or nucleic acid in the sample, and
 (c) identifying the individual as likely to respond to treatment with a kinase inhibitor when one or more of the DDR2 mutations is present, thereby indicating the individual is likely to respond to treatment with a kinase inhibitor.

The DDR2 mutation may be a DDR2 protein mutation selected from the group consisting of R105C, P321L, R458H, S467F, P476S, I488S, F574C, S667F, S674F, R680L, L701F, R742Q, and T836A or a nucleic acid encoding a DDR2 protein having a mutation selected from the group consisting of R105C, P321L, R458H, S467F, P476S, I488S, F574C, S667F, S674F, R680L, L701F, R742Q, and T836A. The presence of any of these mutations may be in an individual with advanced stage melanoma.

The method further may comprise detecting the presence of a BRAF mutation such as V600E or V600K in BRAF from the individual.

In some embodiments, the DDR2 mutation is a DDR2 protein mutation selected from the group consisting of N146K, R399Q, and S702F; or a DDR2 nucleotide sequence encoding a DDR2 mutation selected from the group consisting of N146K, R399Q, and S702F. The presence of any of these mutations may be in an individual with basal cell carcinoma.

In one embodiment, the step of analyzing a biological sample comprises sequencing the DDR2 gene for the presence of mutations known to confer sensitivity to DDR2 inhibitors. In some embodiments, the DDR2 nucleic acid sequence is examined for one or more mutations encoding N146K, R399Q, S702F, R105C, P321L, R458H, S467F, P476S, I488S, F574C, S667F, S674F, R680L, L701F, R742Q, or T836A in DDR2.

Methods of identifying an individual having melanoma or basal cell carcinoma as a candidate for therapy with a DDR2 inhibitor are also disclosed. In some embodiments, a method of identifying an individual having melanoma or basal cell carcinoma as a candidate for therapy with a DDR2 inhibitor, comprises sequencing the DDR2 gene for the presence of mutations known to confer sensitivity to DDR2 kinase inhibitors. In some embodiments, the DDR2 sequence is examined for a sequence encoding at least one mutation selected from the group consisting of R105C, P321L, R458H, S467F, P476S, I488S, F574C, S667F, S674F, R680L, L701F, R742Q and T836A. In an alternate method, the candidate for therapy with a DDR2 inhibitor is identified by the expression levels of DDR2, wherein low expression levels of DDR2 such as GAPDH-normalized relative DDR2 transcript levels below 0.025 indicate the individual is a candidate for therapy.

The invention comprises a method for treating melanoma or basal cell carcinoma in an individual comprising administering to the individual a therapeutically effective amount of a DDR2 inhibitor. In some embodiments, the melanoma is advanced stage melanoma. Suitable DDR2 inhibitors include kinase inhibitors, siRNA, shRNA, and an antibody that specifically binds to DDR2 or to a DDR2 having at least one mutation selected from the group consisting of R105C, P321L, R458H, S467F, P476S, I488S, F574C, S667F, S674F, R680L, L701F, R742Q, and T836A. In some embodiments, the DDR2 inhibitor is a tyrosine kinase inhibitor that inhibits kinase activity of DDR2. In some embodiments, the kinase inhibitor inhibits tyrosine kinase activity of DDR2 having at least one mutation in the kinase domain. In some embodiments, the kinase inhibitor inhibits tyrosine kinase activity of DDR2 having at least one mutation in the discoidin (DS) domain. In some embodiments, the tyrosine kinase inhibitor inhibits kinase activity of DDR2 having at least one mutation selected from the group consisting of R105C, P321L, R458H, S467F, P476S, I488S, F574C, S667F, S674F, R680L, L701F, R742Q, and T836A.

Methods disclosed herein may be used to treat melanoma or basal cell carcinoma in an individual with a DDR2 mutation selected from the group consisting of a mutation in the DDR2 discoidin domain, a mutation in the DDR2 intracellular interacting domain, and a mutation in the DDR2 kinase domain. The DDR2 mutation may be a germline mutation or a somatic cell mutation. In some embodiments the DDR2 mutation is a N146K, R399Q, or S702F mutation. The DDR2 mutation may be encoded by a mutated DDR2 gene.

In relation to therapy, the individual may be examined for mutations in DDR2 protein, comprising sequencing a DDR2 nucleic acid from the individual to determine if the nucleic acid encodes a DDR2 protein with a mutation, and subsequently the likelihood that the individual will respond to therapy with a DDR2 inhibitor. In particular embodiments, the DDR2 sequence of the individual may be determined before the start of treatment or during treatment.

An individual with melanoma or basal cell carcinoma may harbor a mutation in a DDR2 nucleic acid sequence and/or a mutation in a BRAF nucleic acid sequence. The mutation may be in the individual's genomic DNA and/or in RNA. In some embodiments, the methods for treating melanoma or basal cell carcinoma disclosed herein are performed in an individual who does not harbor a mutation in a DDR2 or a BRAF nucleic acid or in an individual carrying a mutated DDR2 and/or BRAF gene or RNA.

In another embodiment, an individual with melanoma or basal cell carcinoma is also treated with a BRAF inhibitor, such as an inhibitor that inhibits activity of BRAF with a mutation at codon 600 (such as a V600E or V600K mutation) or other sensitive BRAF mutations in addition to being treated with a DDR2 inhibitor. Suitable BRAF inhibitors include BRAF kinase inhibitors such as, for example, vemurafenib, GDC-0879, PLX-4720, sorafenib tosylate, dabrafenib, and LGX818.

Compositions for treating melanoma and/or basal cell carcinoma also are provided. In one embodiment, a composition for the treatment of melanoma or basal cell carcinoma comprises a DDR2 inhibitor alone, or with a BRAF inhibitor. The DDR2 inhibitor may be a kinase inhibitor or one or more inhibitors selected from the group consisting of siRNA directed to a DDR2 nucleic acid, shRNA directed to a DDR2 nucleic acid, and an antibody that specifically binds to a DDR2 polypeptide and inhibits DDR2 kinase activity. In some embodiments, the DDR2 kinase inhibitor inhibits DDR2 having mutations in the kinase domain. In some embodiments, the inhibitor inhibits DDR2 having mutations in the discoidin domain. In some embodiments, the composition comprises a DDR2 kinase inhibitor that inhibits kinase activity of DDR2 having one or more of R105C, P321L, R458H, S467F, P476S, I488S, F574C, S667F, S674F, R680L, L701F, R742Q and T836A mutations. The BRAF inhibitor may be, for example, a kinase inhibitor such as vemurafenib, GDC-0879, PLX-4720, sorafenib tosylate, dabrafenib, and LGX818.

The invention also includes kits. For example, a kit for identifying the presence of DDR2 and/or BRAF mutations, the kit comprising at least one primer selected from

| | | |
|---|---|---|
| Exon3F | TCCAGTTCCAACACCATCTTC | (SEQ ID NO: 1) |
| Exon 4F | TTTCTCTTTGGTTTCTCTTGGTC | (SEQ ID NO: 2) |
| Exon 5-1F | CCCAACCCTCACCTCTCAAG | (SEQ ID NO: 3) |
| Exon 5-2F | CCAGTGGAACCTGATGACCT | (SEQ ID NO: 4) |
| Exon 5-3F | CCATGCAGGAGGTCATGG | (SEQ ID NO: 5) |
| Exon 6-1F | CACTCATTCTCTTCTCTCCTCA | (SEQ ID NO: 6) |
| Exon6-2F | CCATTGTAGCCAGATTTGTCC | (SEQ ID NO: 7) |
| Exon 7F | CTTGGCTGTGTTTCCTTTGC | (SEQ ID NO: 8) |
| exon 8-1F | CTCTTCTCCTGGCCTGAGC | (SEQ ID NO: 9) |
| Exon 8-2F | CCCAGACCCATGAATACCAC | (SEQ ID NO: 10) |
| Exon 9-1F | TCACATGCCTCTTTCTCTACCA | (SEQ ID NO: 11) |
| Exon 9-2F | CAGTGCTACTTCCGCTCTGA | (SEQ ID NO: 12) |
| Exon 9-3F | CCCAGTGCTCGGTTTGTC | (SEQ ID NO: 13) |
| Exon 10F | GCTCTGACTCACCCTTGTTTT | (SEQ ID NO: 14) |
| Exon 11-1F | CCTTCTCTCCCTGGTCACAG | (SEQ ID NO: 15) |
| Exon 11-2F | GGATCCTGATTGGCTGCTT | (SEQ ID NO: 16) |
| Exon 12-1F | TCTCCTTGCTCTTCTCTTCCA | (SEQ ID NO: 17) |
| Exon 12-2F | ACCGCTCCTCATCACCTAGT | (SEQ ID NO: 18) |
| exon 13-1F | CTCGTTGCCCTTGTCTTCC | (SEQ ID NO: 19) |
| Exon 13-2F | GAGGGGGTGCCCCACTAT | (SEQ ID NO: 20) |
| Exon 13-3F | AGTGCCTGCCGTCACCAT | (SEQ ID NO: 21) |
| exon 14-1F | TGATGCTGAGACTAGATGACTTTTG | (SEQ ID NO: 22) |
| Exon14-2F | GGGAATGGAAAAATTCAAAGA | (SEQ ID NO: 23) |
| exon 15-1F | TTTATCTATGTCTGTATCCTCCCAAG | (SEQ ID NO: 24) |
| Exon 15-2F | CCATCTATTAGCTGTGTGTATCACTG | (SEQ ID NO: 25) |
| Exon 16-1F | CCTTCTGTCTTCTTGTCTATTTCCTC | (SEQ ID NO: 26) |
| Exon 16-2F2 | TCTCTTAATTTTGTTCACCGAGA | (SEQ ID NO: 27) |
| Exon 16-3F2 | CTTTGGAATGAGCAGGAACC | (SEQ ID NO: 28) |
| Exon 17-1F | TGATTTCCCATTCTTTTCTTTACTT | (SEQ ID NO: 29) |
| Exon 17-2F | TTTGTGGGAGACTTTCACCTTT | (SEQ ID NO: 30) |

| | | |
|---|---|---|
| Exon 18-1F | TTTCCTTTATTTTGTTCCCAAAG | (SEQ ID NO: 31) |
| Exon 18-2F | GCTGCTGGAGAAGAGATACGA | (SEQ ID NO: 32) |
| BRAF 11-1F | TCTGTTTGGCTTGACTTGACTT | (SEQ ID NO: 33) |
| BRAF 11-2F | GACGGGACTCGAGTGATGAT | (SEQ ID NO: 34) |
| Exon 12-1R | GCGATCGTAAGTCGAGTTGG | (SEQ ID NO: 35) |
| Exon 12-2R | CCCACCACATCATCCTCAC | (SEQ ID NO: 36) |
| exon 13-1R | TGTGTTGCCTCCTGTCACTC | (SEQ ID NO: 37) |
| Exon 13-2R | TGGGGAACTCCTCCACAG | (SEQ ID NO: 38) |
| Exon 13-3R | AAGGGAATCAAAGAATCAACTCA | (SEQ ID NO: 39) |
| exon 14-1R | GCTCGGAGCATTTTCACA | (SEQ ID NO: 40) |
| Exon14-2R | GGAAAATTCAAAATGTAGACCACAG | (SEQ ID NO: 41) |
| exon 15-1R | CATGTATTCAGTGATCATACAGAGAGG | (SEQ ID NO: 42) |
| Exon 15-2R | AGAAGGAAGACCTGGCTTGTT | (SEQ ID NO: 43) |
| Exon 16-1R | TGTGTAGTTCTTACCCACTAAACAGT | (SEQ ID NO: 44) |
| Exon 16-2R2 | GCCCTGGATCCGGTAATAGT | (SEQ ID NO: 45) |
| Exon 16-3R2 | CAGGGCTTTAAAATGCTGAGA | (SEQ ID NO: 46) |
| Exon 17-1R | TCTGACAGCTGGGAATAGGG | (SEQ ID NO: 47) |
| Exon 17-2R | CCATTCATCCCCAACAGTTC | (SEQ ID NO: 48) |
| Exon 18-1R | GCAGAAGGTGGATTTCTTGG | (SEQ ID NO: 49) |
| Exon 18-2R | AGGACCTGAGCCGTAGGAAC | (SEQ ID NO: 50) |
| BRAF 11-1R | TCCAATTCTTTGTCCCACTG | (SEQ ID NO: 51) |
| BRAF 11-2R | TGTCACAATGTCACCACATTACA | (SEQ ID NO: 52) |
| BRAF 15-1R | GACCCACTCCATCGAGATTT and | (SEQ ID NO: 53) |
| BRAF 15-2R | TCAGTGGAAAAATAGCCTCAA | (SEQ ID NO: 54) |

BRIEF DESCRIPTION OF THE DRAWINGS

FIGS. 1A-1B are a sequence alignment of the DDR2 protein (top lines) compared with DDR1 (bottom) showing conserved sequence between the two proteins at the sites of DDR2 mutations seen in extracellular-DS domains (amino acids 22-399) and the kinase domain (amino acids 563 to 849) including F574C, S667F, R680L, L701F, R742Q and T836A. FIGS. 1A-1B disclose SEQ ID NOS 89-90, respectively, in order of appearance.

FIG. 2 discloses the first column of sequences on the left, reading top to bottom, as SEQ ID NOS 91-93, 91, 91, 91, 91, 94, 91, 93, 95, 91, 96, 93, 91, 91, 91, 93, 91 and 97-115, the column of sequences in the middle, reading top to bottom, as SEQ ID NOS 116-117, 116, 116, 118, 116, 118, 116, 119, 116, 116, 118, 116, 116, 118, 118, 118, 118, 116, 120, 117 and 121-137, and the last column of sequences on the right, reading top to bottom as SEQ ID NOS 138-139, 138, 138, 138, 140, 140, 138, 138, 141, 140, 138, 138, 138, 138, 138, 138, 142-143, 138 and 144-160, all respectively, in order of appearance.

FIG. 4 discloses SEQ ID NOS 161-163, 161, 161 and 161, respectively, in order of appearance.

FIG. 5 discloses SEQ ID NOS 164-166, 164, 164, 164, 167-169, 167, 167 and 167, respectively, in order of appearance.

DETAILED DESCRIPTION

Definitions

Figure 2:
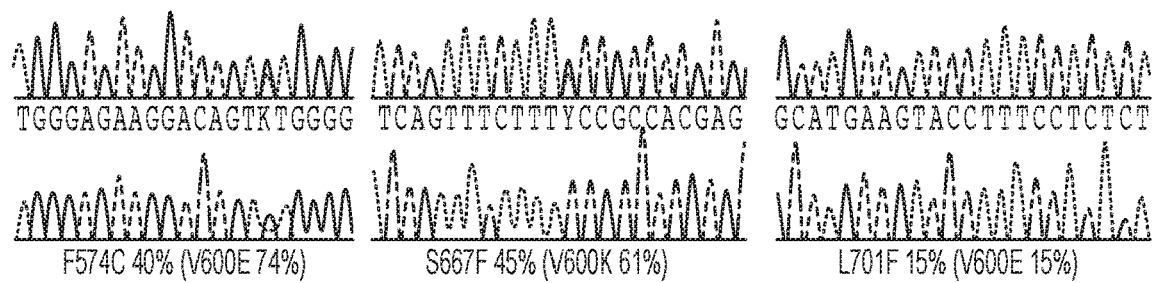
FIG. 2 shows a sequence alignment of three mutations in the DDR2 kinase domain, F574C, S667F and L701F, identified by Ion Torrent sequencing of genomic DNA extracted from macrodissected formalin-fixed paraffin-embedded (FFPE) sections of melanomas; middle panels show mutation confirmations by bidirectional Sanger sequencing; bottom panels show alignment of the mutations in the DDR2 kinase domain with the homologous locations in other kinases, including BRAF, EGFR and ALK.

Certain terms employed in this description have the following defined meanings. Terms that are not defined have their art-recognized meanings. That is, unless otherwise defined, all technical and scientific terms used herein have the same meaning as commonly understood by one of ordinary skill in the art to which this invention belongs.

As used herein, unless otherwise stated, the singular forms "a," "an," and "the" also include the plural. Thus, for example, a reference to "an oligonucleotide" includes a plurality of oligonucleotide molecules, a reference to label is a reference to one or more labels, a reference to probe is a reference to one or more probes, and a reference to "a nucleic acid" is a reference to one or more polynucleotides.

As used herein, unless indicated otherwise, when referring to a numerical value, the term "about" means plus or minus 10% of the enumerated value.

As used herein, the terms "isolated," "purified" or "substantially purified" refer to molecules, such as nucleic acid, that are removed from their natural environment, isolated or separated, and are at least 60% free, preferably 75% free, and most preferably 90% free from other components with which they are naturally associated. An isolated molecule is therefore a substantially purified molecule.

A "fragment" in the context of a gene fragment or a chromosome fragment refers to a sequence of nucleotide residues which are at least about 10 nucleotides, at least about 20 nucleotides, at least about 25 nucleotides, at least about 30 nucleotides, at least about 40 nucleotides, at least about 50 nucleotides, at least about 100 nucleotides, at least about 250 nucleotides, at least about 500 nucleotides, at least about 1,000 nucleotides, at least about 2,000 nucleotides.

The terms "identity" and "identical" refer to a degree of identity between sequences. There may be partial identity or complete identity. A partially identical sequence is one that is less than 100% identical to another sequence. Partially identical sequences may have an overall identity of at least 70% or at least 75%, at least 80% or at least 85%, or at least 90% or at least 95%.

The term "detectable label" as used herein refers to a molecule or a compound or a group of molecules or a group of compounds associated with a probe and is used to identify the probe hybridized to a genomic nucleic acid or reference nucleic acid.

As used herein, the term "detecting" refers to observing a signal from a detectable label to indicate the presence of a target. More specifically, detecting is used in the context of detecting a specific sequence.

The term "multiplex PCR" as used herein refers to an assay that provides for simultaneous amplification and detection of two or more products within the same reaction vessel. Each product is primed using a distinct primer pair. A multiplex reaction may further include specific probes for each product that are detectably labeled with different detectable moieties.

The term "nested polymerase chain reaction" is a modification of polymerase chain reaction which, in the present context, is performed to add sequences to an amplicon. Nested polymerase chain reaction involves two sets of primers, used in two successive runs of polymerase chain reaction, the second set intended to amplify the target from the first run product.

As used herein, the term "oligonucleotide" refers to a short polymer composed of deoxyribonucleotides, ribonucleotides, or any combination thereof. Oligonucleotides are generally between about 10, 11, 12, 13, 14, 15, 20, 25, or 30 to about 150 nucleotides (nt) in length, more preferably about 10, 11, 12, 13, 14, 15, 20, 25, or 30 to about 70 nt As used herein, the term "subject" or "individual" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like).

The terms "complement," "complementary" or "complementarity" as used herein with reference to polynucleotides (i.e., a sequence of nucleotides such as an oligonucleotide or a genomic nucleic acid) related by the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, for the sequence 5'-A-G-T-3' is complementary to the sequence 3'-T-C-A-5'. Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. Complementarity may be "partial" in which only some of the nucleic acids' bases are matched according to the base pairing rules. Or, there may be "complete," "total," or "full" complementarity between the nucleic acids.

"Detecting" a mutation in a gene or protein may be accomplished by performing an appropriate assay. To detect a mutation in a gene or protein in a biological sample, the biological sample is assayed to determine the presence or absence of the mutated gene or mutated protein. The assay may include extracting nucleic acid (such as, for example, total genomic DNA and/or RNA) from the sample and analyzing the extracted nucleic acid by methods known in the art. An assay may involve isolating protein from the biological sample and analyzing the protein. However, an assay need not involve either extraction of nucleic acid or isolation of protein. That is, some assays may be employed that directly analyze a biological sample without extracting or isolating nucleic acid or protein.

Methods of Diagnosis

In one embodiment, a method for diagnosing melanoma in an individual is described, comprising (a) analyzing a biological sample from the individual, (b) detecting the presence of a DDR2 protein having a mutation selected from the group consisting of R105C, P321L, R458H, S467F, P476S, I488S, F574C, S667F, S674F, R680L, L701F, R742Q, and T836A or a nucleic acid encoding such a DDR2 protein in the sample, and (c) diagnosing the individual as having melanoma when the mutation is detected, thereby indicating that the individual has melanoma. The melanoma may be a particular subset of melanoma. In some embodiments, the method is for diagnosing advanced stage melanoma.

Methods for diagnosing basal cell carcinoma in an individual are also disclosed. A method for diagnosing basal cell carcinoma in an individual, comprises (a) analyzing a biological sample from the individual, (b) detecting the presence of a DDR2 protein having a mutation selected from the group consisting of N146K, R399Q, and S702F, or a DDR2 nucleic acid that encodes the mutated DDR2 protein in the sample, and (c) identifying the individual as having basal cell carcinoma when the mutation is present, thereby indicating the individual has basal cell carcinoma.

The nucleic acid may be DNA and/or RNA.

Methods of diagnosis may be performed in an individual with a skin lesion. A "skin lesion" is an area of variation in skin color and/or texture. Alternatively or in addition, the individual may be suspected of having a skin disorder such as, for example, skin cancer, melanoma or basal cell carcinoma.

Methods of Screening/Predicting Response to Treatment

Another aspect of the present invention provides a method for determining likelihood of responding to treatment with a kinase inhibitor in an individual with melanoma or basal cell carcinoma, comprising: (a) analyzing a biological sample from the individual to detect the presence of a DDR2 mutation that confers sensitivity to a kinase inhibitor, and (b) identifying the individual as likely to respond to treatment with a kinase inhibitor when one or more DDR2 mutations is present, thereby indicating the individual is likely to respond to treatment with a kinase inhibitor. In some embodiments, the DDR2 mutation is an amino acid mutation in a DDR2 protein selected from the group consisting of R105C, P321L, R458H, S467F, P476S, I488S, F574C, S667F, S674F, R680L, L701F, R742Q and T836A. In other embodiments, the DDR2 mutation is a nucleic acid sequence encoding a DDR2 protein having a mutation selected from the group consisting of R105C, P321L, R458H, S467F, P476S, I488S, F574C, S667F, S674F, R680L, L701F, R742Q, and T836A.

In some embodiments the DDR2 mutation is a DDR2 protein mutation selected from the group consisting of N146K, R399Q, and S702F. In some embodiments the DDR2 mutation is a DDR2 nucleic acid sequence encoding a DDR2 mutation selected from the group consisting of N146K, R399Q, and S702F.

The method further may comprise detecting the presence of a V600E or V600K mutation in BRAF from the individual. The individual may have advanced stage melanoma.

Yet another aspect of the present invention discloses a method for stratifying early and late stage melanoma, comprising (a) analyzing a biological sample from an individual with melanoma or suspected of having melanoma, (b) detecting the presence of a DDR2 mutation, such as R105C, P321L, R458H, S467F, P476S, I488S, F574C, S667F, S674F, R680L, L701F, R742Q or T836A in the sample, and (c) identifying the melanoma as later stage when the DDR2 mutation is detected. The presence of these mutations is indicative of later stage melanoma given their absence in primary cutaneous melanomas and their presence in secondary cutaneous nodules or metastatic lesions which have adverse prognosis (Balch C M et al. Prognostic Factors Analysis of 17,600 Melanoma Patients: Validation of the American Joint Committee on Cancer Melanoma Staging System. JCO Aug. 15, 2001 vol. 19 no. 16 3622-3634, Balch C M et al. Final Version of 2009 AJCC Melanoma Staging and Classification. JCO Dec. 20, 2009 vol. 27 no. 36 6199-6206).

In one aspect of the present invention, an individual is identified as likely to respond to therapy with a DDR2 inhibitor such as, for example, a DDR2 kinase inhibitor, when GAPDH-normalized relative DDR2 transcript levels in a biological sample from the individual are below 0.025.

The term "biological sample" as used herein refers to a sample containing a nucleic acid of interest. A biological sample may comprise a clinical sample (i.e., obtained directly from a patient) or isolated nucleic acids and may be cellular or acellular fluids and/or tissue (e.g., biopsy) samples. In some embodiments, a sample is obtained from a tissue or bodily fluid collected from a subject. Sample sources include, but are not limited to, sputum (processed or unprocessed), bronchial alveolar lavage (BAL), bronchial wash (BW), whole blood or isolated blood cells of any type (e.g., lymphocytes), bodily fluids, cerebrospinal fluid (CSF), urine, plasma, serum, or tissue (e.g., biopsy material). Methods of obtaining test samples and reference samples are well known to those of skill in the art and include, but are not limited to, aspirations, tissue sections, drawing of blood or other fluids, surgical or needle biopsies, collection of paraffin embedded tissue, collection of body fluids, collection of stool, and the like. In the present context the biological sample preferably is blood, serum or plasma. The term "patient sample" as used herein refers to a sample obtained from a human seeking diagnosis and/or treatment of a disease, especially prostate disease.

To detect the presence of a DDR2 or BRAF mutation, nucleic acid samples or target nucleic acids may be amplified and sequenced by various methods known to the skilled artisan including Sanger sequencing and so-called Next Generation Sequencing (NGS). Next-generation sequencing lowers the costs and greatly increases the speed over the industry standard dye-terminator methods. Examples of NGS include (a) Massively Parallel Signature Sequencing (MPSS)
(b) Polony sequencing combined an in vitro paired-tag library with emulsion PCR
(c) 454 pyrosequencing
(d) Solexa sequencing
(e) SOLiD technology
(f) DNA nanoball
(g) Heliscope single molecule
(h) Single molecule real time (SNRT) and
(i) Ion semiconductor sequencing Ion semiconductor sequencing couples standard sequencing chemistry with a novel, semiconductor based detection system that detects hydrogen ions that are released during the polymerization of DNA, as opposed to the optical methods used in other sequencing systems. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogens and a proportionally higher electronic signal.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplification product," also known as an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al., Eds., Academic Press, San Diego, Calif. 1990, pp. 13-20; Wharam et al., *Nucleic Acids Res.*, 29(11):E54-E54, 2001; Hafner et al., *Biotechniques*, 30(4):852-56, 858, 860, 2001; Zhong et al., *Biotechniques*, 30(4):852-6, 858, 860, 2001.

A key feature of PCR is "thermocycling" which, in the present context, comprises repeated cycling through at least three different temperatures: (1) melting/denaturation, typically at 95° C. (2) annealing of a primer to the target DNA at a temperature determined by the melting point (Tm) of the region of homology between the primer and the target and (3) extension at a temperature dependent on the polymerase, most commonly 72° C. These three temperatures are then repeated numerous times. Thermocycling protocols typically also include a first period of extended denaturation, and end on an extended period of extension.

The Tm of a primer varies according to the length, G+C content, and the buffer conditions, among other factors. As used herein, Tm refers to that in the buffer used for the reaction of interest.

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the Tm of the formed hybrid.

Methods of Treatment

In one aspect of the invention, a method of treating melanoma or basal cell carcinoma in an individual comprises administering to the individual a therapeutically effective amount of a DDR2 inhibitor. A "DDR2 inhibitor" is a compound that inhibits DDR2 function (including DDR2 kinase activity) and includes kinase inhibitors that inhibit DDR2 kinase activity as well as siRNA specific for DDR2 nucleic acid, shRNA specific for DDR2 nucleic acid and an antibody that binds to DDR2 and inhibits associated DDR2 kinase activity.

An "antibody" includes a polyclonal antibody, a monoclonal antibody, an antigen-binding fragments thereof such as F(ab').sub.2 and an Fab fragments, and a single chain antibody.

As used herein, a "kinase inhibitor" is a composition that inhibits kinase activity of a protein kinase. A "tyrosine kinase inhibitor" is a composition that inhibits tyrosine kinase activity of a protein tyrosine kinase, and a "serine/threonine kinase inhibitor" is a compound that inhibits serine/threonine kinase activity of a protein serine/threonine kinase. Exemplary kinase inhibitors include imatinib, nilotinib, dasatinib, GDC-0879, PLX-4720, sorafenib, tosylate, dabrafenib, vemurafenib and LGX818. Imatinib mesylate (also known as STI571 or 2-phenylaminopyrimidine or "imantinib" for short; marketed as a drug under the trade name "Gleevec" or "Glivec") is an ATP competitive inhibitor of tyrosine kinase activity. Other kinase inhibitor drugs include bosutinib (SKI-606) and the aurora kinase inhibitor VX-680.

A "DDR2 kinase inhibitor" is a compound that inhibits DDR2 kinase activity, including kinase activity of a DDR2 having at least one mutation selected from the group consisting of R105C, P321L, R458H, S467F, P476S, I488S, F574C, S667F, S674F, R680L, L701F, R742Q, T836A, N146K, R399Q, and S702F. A DDR2 kinase inhibitor may kinase inhibit activity of a DDR2 protein directly, or it may act upstream by inhibiting DDR2 nucleic acid (e.g., by inhibiting transcription or translation). Exemplary DDR2 kinase inhibitors include imatinib, nilotinib and dasatinib.

In one embodiment of this aspect of the invention, the method comprises administering to the individual a therapeutically effective amount of a BRAF inhibitor, in addition to the DDR2 inhibitor. A "BRAF inhibitor" is any compound that inhibits BRAF function (including BRAF kinase activity) and includes kinase inhibitors that inhibit BRAF kinase activity as well as siRNA specific for BRAF nucleic acid, shRNA specific for BRAF nucleic acid and antibodies that bind to BRAF and inhibit associated BRAF kinase activity. The BRAF inhibitor may be a serine/threonine kinase inhibitor. A "BRAF kinase inhibitor" is a compound that inhibits BRAF kinase activity. Exemplary BRAF kinase inhibitors include GDC-0879, PLX-4720, sorafenib, vemurafenib, tosylate, dabrafenib, and LGX818

Routes and frequency of administration of the therapeutic agents disclosed herein, as well as dosage, will vary from individual to individual as well as with the selected drug, and may be readily established using standard techniques. In general, the pharmaceutical compositions may be administered, by injection (e.g., intracutaneous, intratumoral, intramuscular, intravenous or subcutaneous), intranasally (e.g., by aspiration) or orally. In a particular embodiment, the pharmaceutical composition is administered orally. In one example, between 1 and 10 doses may be administered over a 52 week period. Preferably, 6 doses are administered, at intervals of 1 month, and booster treatments may be given periodically thereafter. Alternate protocols may be appropriate for individual patients. In one embodiment, 2 intradermal injections of the composition are administered 10 days apart.

A "solid oral dosage form," "oral dosage form," "unit dose form," "dosage form for oral administration," and the like are used interchangably, and refer to a pharmaceutical composition in the form of a tablet, capsule, caplet, gelcap, geltab, pill and the like.

Dosage forms typically include an "excipient," which as used herein, is any component of an dosage form that is not an API. Excipients include binders, lubricants, diluents, disintegrants, coatings, barrier layer components, glidants, and other components. Excipients are known in the art (see HANDBOOK OF PHARMACEUTICAL EXCIPIENTS, FIFTH EDITION, 2005, edited by Rowe et al., McGraw Hill). Some excipients serve multiple functions or are so-called high functionality excipients. For example, talc may act as a lubricant, and an anti-adherent, and a glidant. See Pifferi et al., 2005, "Quality and functionality of excipients" Farmaco. 54:1-14; and Zeleznik and Renak, Business Briefing: Pharmagenerics 2004.

A suitable dose is an amount of a compound that, when administered as described above, is capable of promoting an anti-cancer immune response, and is at least 10-50% above the basal (i.e., untreated) level. Such response can be monitored using conventional methods. In general, for pharmaceutical compositions, the amount of each drug present in a dose ranges from about 100 µg to 5 mg per kg of host, but those skilled in the art will appreciate that specific doses depend on the drug to be administered and are not necessarily limited to this general range. Likewise, suitable volumes for each administration will vary with the size of the patient.

In the context of treatment, a "therapeutically effective amount" of a drug is an amount of or its pharmaceutically acceptable salt which eliminates, alleviates, or provides relief of the symptoms for which it is administered. The disclosed compositions are administered in any suitable manner, often with pharmaceutically acceptable carriers. Suitable methods of administering treatment in the context of the present invention to a subject are available, and, although more than one route can be used to administer a particular composition, a particular route can often provide a more immediate and more effective reaction than another route. The dose administered to a patient, in the context of the present invention, should be sufficient to effect a beneficial therapeutic response in the patient over time, or to inhibit disease progression. Thus, the composition is administered to a subject in an amount sufficient to elicit an effective response and/or to alleviate, reduce, cure or at least partially arrest symptoms and/or complications from the disease. An amount adequate to accomplish this is defined as a "therapeutically effective dose."

In general, an appropriate dosage and treatment regimen involves administration of the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients.

In some embodiment, IC50 for inhibition of wild-type DDR2 kinase activity is in the range of 600 nM for imatinib, 50 nM for nilotinib and 1.5 nM for dasatinib (Day E, et al. Inhibition of collagen-induced discoidin domain receptor 1 and 2 activation by imatinib, nilotinib and dasatinib. Molec Cell Pharm 2008; 599:44-53), which are below the achievable plasma trough concentrations of the drugs in their current daily oral dosing (4 uM, 2 uM and 100 nM respectively, see Bradeen et al. Blood 2006; 108:2332-2338).

The DDR2 inhibitor and BRAF inhibitor, if both administered, can be administered sequentially or concurrently, and may be formulated separately or as a single composition.

Kits

In one embodiment of the invention, a kit may be used for conducting the diagnostic and prognostic methods described herein. Typically, the kit should contain, in a carrier or compartmentalized container, reagents useful in any of the above-described embodiments of the diagnostic method. The carrier can be a container or support, in the form of, e.g., bag, box, tube, rack, and is optionally compartmentalized. The carrier may define an enclosed confinement for safety purposes during shipment and storage. A kit as disclosed herein may contain printed or electronic instructions for performing an assay that employs the reagents contained in the kit. In one embodiment, the kit includes one or more PCR primers capable of amplifying and sequencing. Relevant primers include

| Exon3F | TCCAGTTCCAACACCATCTTC | (SEQ ID NO: 1) |
| Exon 4F | TTTCTCTTTGGTTTCTCTTGGTC | (SEQ ID NO: 2) |
| Exon 5-1F | CCCAACCCTCACCTCTCAAG | (SEQ ID NO: 3) |
| Exon 5-2F | CCAGTGGAACCTGATGACCT | (SEQ ID NO: 4) |
| Exon 5-3F | CCATGCAGGAGGTCATGG | (SEQ ID NO: 5) |
| Exon 6-1F | CACTCATTCTCTTCTCTCCTCA | (SEQ ID NO: 6) |
| Exon6-2F | CCATTGTAGCCAGATTTGTCC | (SEQ ID NO: 7) |
| Exon 7F | CTTGGCTGTGTTTCCTTTGC | (SEQ ID NO: 8) |
| exon 8-1F | CTCTTCTCCTGGCCTGAGC | (SEQ ID NO: 9) |
| Exon 8-2F | CCCAGACCCATGAATACCAC | (SEQ ID NO: 10) |
| Exon 9-1F | TCACATGCCTCTTTCTCTACCA | (SEQ ID NO: 11) |
| Exon 9-2F | CAGTGCTACTTCCGCTCTGA | (SEQ ID NO: 12) |

| | | |
|---|---|---|
| Exon 9-3F | CCCAGTGCTCGGTTTGTC | (SEQ ID NO: 13) |
| Exon 10F | GCTCTGACTCACCCTTGTTTT | (SEQ ID NO: 14) |
| Exon 11-1F | CCTTCTCTCCCTGGTCACAG | (SEQ ID NO: 15) |
| Exon 11-2F | GGATCCTGATTGGCTGCTT | (SEQ ID NO: 16) |
| Exon 12-1F | TCTCCTTGCTCTTCTCTTCCA | (SEQ ID NO: 17) |
| Exon 12-2F | ACCGCTCCTCATCACCTAGT | (SEQ ID NO: 18) |
| exon 13-1F | CTCGTTGCCCTTGTCTTCC | (SEQ ID NO: 19) |
| Exon 13-2F | GAGGGGGTGCCCCACTAT | (SEQ ID NO: 20) |
| Exon 13-3F | AGTGCCTGCCGTCACCAT | (SEQ ID NO: 21) |
| exon 14-1F | TGATGCTGAGACTAGATGACTTTTG | (SEQ ID NO: 22) |
| Exon14-2F | GGGAATGGAAAAATTCAAAGA | (SEQ ID NO: 23) |
| exon 15-1F | TTTATCTATGTCTGTATCCTCCCAAG | (SEQ ID NO: 24) |
| Exon 15-2F | CCATCTATTAGCTGTGTGTATCACTG | (SEQ ID NO: 25) |
| Exon 16-1F | CCTTCTGTCTTCTTGTCTATTTCCTC | (SEQ ID NO: 26) |
| Exon 16-2F2 | TCTCTTAATTTTGTTCACCGAGA | (SEQ ID NO: 27) |
| Exon 16-3F2 | CTTTGGAATGAGCAGGAACC | (SEQ ID NO: 28) |
| Exon 17-1F | TGATTTCCCATTCTTTTCTTTACTT | (SEQ ID NO: 29) |
| Exon 17-2F | TTTGTGGGAGACTTTCACCTTT | (SEQ ID NO: 30) |
| Exon 18-1F | TTTCCTTTATTTTTGTTCCCAAAG | (SEQ ID NO: 31) |
| Exon 18-2F | GCTGCTGGAGAAGAGATACGA | (SEQ ID NO: 32) |
| BRAF 11-1F | TCTGTTTGGCTTGACTTGACTT | (SEQ ID NO: 33) |
| BRAF 11-2F | GACGGGACTCGAGTGATGAT | (SEQ ID NO: 34) |
| Exon 12-1R | GCGATCGTAAGTCGAGTTGG | (SEQ ID NO: 35) |
| Exon 12-2R | CCCACCACATCATCCTCAC | (SEQ ID NO: 36) |
| exon 13-1R | TGTGTTGCCTCCTGTCACTC | (SEQ ID NO: 37) |
| Exon 13-2R | TGGGGAACTCCTCCACAG | (SEQ ID NO: 38) |

| | | |
|---|---|---|
| Exon 13-3R | AAGGGAATCAAAGAATCAACTCA | (SEQ ID NO: 39) |
| exon 14-1R | GCTCGGAGCATTTTCACA | (SEQ ID NO: 40) |
| Exon14-2R | GGAAAATTCAAAATGTAGACCACAG | (SEQ ID NO: 41) |
| exon 15-1R | CATGTATTCAGTGATCATACAGAGAGG | (SEQ ID NO: 42) |
| Exon 15-2R | AGAAGGAAGACCTGGCTTGTT | (SEQ ID NO: 43) |
| Exon 16-1R | TGTGTAGTTCTTACCCACTAAACAGT | (SEQ ID NO: 44) |
| Exon 16-2R2 | GCCCTGGATCCGGTAATAGT | (SEQ ID NO: 45) |
| Exon 16-3R2 | CAGGGCTTTAAAATGCTGAGA | (SEQ ID NO: 46) |
| Exon 17-1R | TCTGACAGCTGGGAATAGGG | (SEQ ID NO: 47) |
| Exon 17-2R | CCATTCATCCCCAACAGTTC | (SEQ ID NO: 48) |
| Exon 18-1R | GCAGAAGGTGGATTTCTTGG | (SEQ ID NO: 49) |
| Exon 18-2R | AGGACCTGAGCCGTAGGAAC | (SEQ ID NO: 50) |
| BRAF 11-1R | TCCAATTCTTTGTCCCACTG | (SEQ ID NO: 51) |
| BRAF 11-2R | TGTCACAATGTCACCACATTACA | (SEQ ID NO: 52) |
| BRAF 15-1R | GACCCACTCCATCGAGATTT and | (SEQ ID NO: 53) |
| BRAF 15-2R | TCAGTGGAAAAATAGCCTCAA | (SEQ ID NO: 54) |

As used herein, a "primer" is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal extension and/or amplification. The term "primer" includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of DNA. A "reverse primer" is complementary to the sense-strand of DNA.

The kit may also include suitable buffers, reagents for isolating nucleic acid, and instructions for use. Kits may also include a microarray for measuring miRNA level.

The primers may be labeled with a detectable marker such as radioactive isotopes, or fluorescence markers. Instructions for using the kit or reagents contained therein are also included in the kit.

EXAMPLES

Example 1: Identification of Novel DDR2 Mutations in Cancer

The following test was conducted, which reports a DETECTED/NOT DETECTED result for any mutation or indels found in the sixteen coding DDR2 exons and in BRAF exons 11 and 15, which are the sites of >99% of the known activating BRAF mutations in identified in melanoma.

Total nucleic acid was extracted from paraffin-embedded tissues in block forms or affixed to slides. For one detection method, thirty six pairs of primers were designed to amplify full coding DDR2 sequences and BRAF exon 11/15 which are located at chromosome 1 and 7 in a microfluidic device, 48.48 Access Array chip. All amplicons from each sample were harvested on the Access Array chip. The pooled amplicons were end-repaired and a unique barcoded A adaptor and a P1 adaptor were ligated onto both ends of amplicons for each sample. The resulting DNA amplicons were the "DNA sequencing library" with a unique barcode sequence for each sample. 12~16 DNA libraries were mixed equally to make a 300 million DNA fragment pool. The emulsion PCR was performed by mixing 1 ml of PCR reaction mixture containing the library pool and Ion Sphere Particle (ISP) and 9 ml of oil. The ISP beads were recovered from emulsion PCR and the template-positive ISPs were enriched, the ISPs were loaded on to a chip for semiconductor sequencing analysis. Sequencing raw data were transferred to the Ion Torrent and processed into next-generation standard sequence formats. The sequence data were aligned and analyzed by Ion Suite Software, SeqNext or NEXTGen software using GenBank accession number NM_006182 as reference. This semi-quantitative test reports a DETECTED/NOT DETECTED result for any mutation or indels found in the sixteen coding DDR2 exons and in BRAF exons 11 and 15, which are the sites of >99% of the known activating BRAF mutations in identified in melanoma.

Approximately 50% of the DDR2 mutations in melanoma were associated with concurrent mutations of the BRAF serine/threonine kinase at codon 600. Based on the mutation levels, DDR2 and BRAF mutations are predicted to be present in most, if not all, of the tumor cells.

These findings suggest that dysregulation by a DDR2 mutation plays a role in melanoma progression because, unlike BRAF mutations, we have not found DDR2 mutations in nevi. This finding is interesting in light of a previous study, which demonstrates that DDR2 downregulation in a melanoma cell line can modulate its metastatic potential (Oncol Rep 2011 October; 26(4):971-8) and mediate cell cycle arrest and the adhesion phenotype of primary tumor cells (Frontiers in Bioscience 10, 2922-2931, Sep. 1, 2005).

TABLE 1

| Controls Used | |
| --- | --- |
| Controls | Supplier and Catalog Number |
| No Primer control in Access Array PCR | |
| DDR2 and BRAF positive heterozygous control serving as a PCR and Ion sequencing control | Previously tested DDR2 and BRAF heterozygous patient samples if available. The Samples may also serve as an unmutated (negative) control in the other remaining exons. |
| DDR2 I638F positive heterozygous control serving as a PCR and Ion sequencing control | ATCC cell line (NCI-H2286) with a known I638F mutation in exon 15. The DNA may also serve as an unmutated (negative) control for the other exons. |
| DDR2 L239R and P815I positive heterozygous control serving as a PCR and Ion sequencing control | DSMZ cell line (HCC366) with a known L239R mutation in exon 8 and a novel P815I mutation in exon 18. The DNA may also serve as an unmutated (negative) control for the other exons. |
| BRAF V600E positive homozygous control a PCR and Ion sequencing control. | ATCC cell line (A375) with a known V600E mutation on exon 15. The DNA may also serve as an unmutated (negative) control for the other exons. |

Example 2

Somatic mutations in DDR2 were identified in melanomas that contained a BRAF V600 mutation. All mutations were detected by Ion Torrent advanced sequencing and then confirmed by bidirectional Sanger sequencing.

This finding may also be useful for distinguishing melanoma from nevi, which can be difficult to distinguish both clinically and histologically.

DDR2 mutations provide a targetable genetic feature in a group of melanomas for tyrosine kinase inhibitors such as imatinib, dasatinib and nilotinib. IC50 for inhibition of

TABLE 2

| Novel DDR2 Somatic Mutations Identified in Melanoma. | | | | | |
| --- | --- | --- | --- | --- | --- |
| DDR2 Mutation Site | Domain location in DDR2 | Conserved residue between DDR kinases | Biopsy Site | Lesion type | BRAF status |
| R105C | Extracellular DS, collagen-binding | Yes | Skin, thigh | 2° nodule | BRAF V600E |
| P321L | Extracellular DS, collagen-binding | No | Skin, scalp | 2° nodule | BRAF V600E BRAF G466V |
| I488S | Cytoplasmic | No | Breast | 2° nodule | BRAF V600K |
| F574C | Kinase | Yes | Skin, abdomen | 2° nodule | BRAF V600E |
| S667F | Kinase | Yes | Lymph node | EC Met | BRAF V600K |
| L701F | Kinase | Yes | Breast | 2° nodule | BRAF V600E |
| DDR2 mutation arising in melanomas without BRAF exon 11 or 15 mutations | | | | | |
| S467F | Cytoplasmic | No | Skin, left wrist | nodule | None |
| P476S | Cytoplasmic | No | Skin, mid-chest | 2° nodule | None |
| S674F | Kinase | Yes | Lung | EC Met | None |
| R680L | Kinase | No | Soft tissue, neck | 2° nodule | None |
| R742Q | Kinase | Yes | Skin, thigh | nodule | None |
| T836A | Kinase | Yes | Lung | EC Met | None |

Novel DDR2 mutations at conserved residues within DDR2 include R105C, P321L, R458H, F574C, S667F and L701F were identified in human malignant melanoma.

wild-type DDR2 kinase activity is in the range of 600 nM for imatinib, 50 nM for nilotinib and 1.5 nM for dasatinib (Day E, et al. Inhibition of collagen-induced discoidin domain receptor 1 and 2 activation by imatinib, nilotinib and dasatinib. Molec Cell Pharm 2008; 599:44-53), which are below the achievable plasma trough concentrations of the drugs in their current daily oral dosing (4 uM, 2 uM and 100 nM respectively, see Bradeen et al. Blood 2006; 108:2332-2338).

Therefore, melanoma may be treated by targeting DDR2 kinase activity along with targeting BRAF kinase activity. This discovery therefore opens up an additional therapeutic option for patients with melanoma.

Example 3

Genomic DNA extracted from FFPE blocks or tissue sections in routine clinical tumor samples can be sequenced by standard PCR-based dideoxy chain termination sequencing ("Sanger" method). Relevant primers include:

TABLE 3

DDR2 PCR/Sequencing Primers

| Name | Sequence | SEQ ID NO |
|---|---|---|
| DR3F | Tgt aaa acg acg gcc agt TGAGAATTGTACTCATTCATGTTGG | (SEQ ID NO: 55) |
| DR3R | cag gaa aca gct atg acc GTAGTCCCTCTTGGCAGCTT | (SEQ ID NO: 56) |
| DR4F | Tgt aaa acg acg gcc agt TCTTATTCCTTGTTCAATATTCAGTG | (SEQ ID NO: 57) |
| DR4R | cag gaa aca gct atg acc CCCCTAGGGTCAGGAATCTG | (SEQ ID NO: 58) |
| DR5F | Tgt aaa acg acg gcc agt CAGCTGCTTGCCTGTGAAC | (SEQ ID NO: 59) |
| DR5R | cag gaa aca gct atg acc CACACAGAAAACCTGTACCCTTC | (SEQ ID NO: 60) |
| DR6F | Tgt aaa acg acg gcc agt GTGGTGGGGTGAAGAAAAGT | (SEQ ID NO: 61) |
| DR6R | cag gaa aca gct atg acc TCCCTTTCTGATTTGATTGC | (SEQ ID NO: 62) |
| DR7F | Tgt aaa acg acg gcc agt CGCTGTGCAAGCTTATACCC | (SEQ ID NO: 63) |
| DR7R | cag gaa aca gct atg acc TTGATTGATTATTGATCCCAAGA | (SEQ ID NO: 64) |
| DR8F | Tgt aaa acg acg gcc agt GAGTGAAGATGCCGGGTAAA | (SEQ ID NO: 65) |
| DR8R | cag gaa aca gct atg acc TGAACTGGCATCAGCCTAGA | (SEQ ID NO: 66) |
| DR9F | Tgt aaa acg acg gcc agt TACTGAGTTGGCTGGCACTG | (SEQ ID NO: 67) |
| DR9R | cag gaa aca gct atg acc TGAGAAGTTCTGGGCATGTG | (SEQ ID NO: 68) |
| DR10F | Tgt aaa acg acg gcc agt TCACTAAATTGATCTTGTAATGTGC | (SEQ ID NO: 69) |
| DR10R | cag gaa aca gct atg acc CCAGGGCTACTCTTCATCCA | (SEQ ID NO: 70) |
| DR11F | Tgt aaa acg acg gcc agt AGGAACAGGGTCTACCTCCA | (SEQ ID NO: 71) |
| DR11R | cag gaa aca gct atg acc AAATGTTTGCAATTTGCCTTTT | (SEQ ID NO: 72) |
| DR12F | Tgt aaa acg acg gcc agt TGGGAGAGCTGAGTTTAAGAAGA | (SEQ ID NO: 73) |
| DR12R | cag gaa aca gct atg acc GCAGAGACTAAAAATAGATGCAATGA | (SEQ ID NO: 74) |
| DR13F | Tgt aaa acg acg gcc agt GCCCTCCTCTCAGAGTTCCT | (SEQ ID NO: 75) |
| DR13R | cag gaa aca gct atg acc GTGAATCCACCTCTGGAAGG | (SEQ ID NO: 76) |

TABLE 3-continued

DDR2 PCR/Sequencing Primers

| | | |
|---|---|---|
| DR14F | Tgt aaa acg acg gcc agt GGAAATGCCCAGCAAGAGTA | (SEQ ID NO: 77) |
| DR14R | cag gaa aca gct atg acc GCTCACTGACCTTCCCATCT | (SEQ ID NO: 78) |
| DR15F | Tgt aaa acg acg gcc agt ATAGGCCTTGGTGTGCATTC | (SEQ ID NO: 79) |
| DR15R | cag gaa aca gct atg acc ACTGACTTCCCCCACCATC | (SEQ ID NO: 80) |
| DR16F | Tgt aaa acg acg gcc agt GAATGTTGAGCTTTCAACCCTA | (SEQ ID NO: 81) |
| DR16R | cag gaa aca gct atg acc AGCCCACAAGCCAGTTGTTA | (SEQ ID NO: 82) |
| DR17F | Tgt aaa acg acg gcc agt AGAATTCCTTGCCTGTGGTG | (SEQ ID NO: 83) |
| DR17R | cag gaa aca gct atg acc AGTGACAAAGACTAACACCTGGA | (SEQ ID NO: 84) |
| DR18F | Tgt aaa acg acg gcc agt CAAATCAAACCATGATGCAAA | (SEQ ID NO: 85) |
| DR18R | cag gaa aca gct atg acc TGTCCAGATGGAGTGGCATA | (SEQ ID NO: 86) |
| M13-F | Tgt aaa acg acg gcc agt | (SEQ ID NO: 87) |
| M13-R | cag gaa aca gct atg acc | (SEQ ID NO: 88) |

M13-F and M13-R are sequencing primers
100 μM (for PCR reaction):
For X mmol of the dry primer (provided by manufacturer), add 10 X μl of nuclease free distilled water.

Example 4

To assess whether DDR2 is mutated or dysregulated in melanoma, we screened DNA extracted from a variety of different melanocytic lesions, focusing particularly on high-stage melanomas that would be candidates for kinase inhibitor therapy.

Mutations in the DDR2 kinase domain, F574C, S667F and L701F, were identified by Ion Torrent sequencing of genomic DNA extracted from macrodissected FFPE sections of primary melanomas. Normalized for pathologist estimates of tumor percentages in the macrodissected areas, all mutations were predicted to be present at heterozygous levels (percentages indicate unnormalized reads of mutant sequence compared to wild-type). Mutations were confirmed by bidirectional Sanger sequencing.

Ion sequencing was performed on the PGM platform on a 316 chip and the 200 base pair sequencing chemistry; emulsion PCR was performed on the OneTouch ES or 2 (all Life Technologies). To produce the library, singleplex PCR was performed on the Access Array system (Fluidigm, South San Francisco, Calif.) using custom-designed primers for 48 amplicons covering the entire coding region of DDR2 and exons 11 and 15 of BRAF. Sequence analysis was performed on SequencePilot software (JSI Medical Systems, Costa Mesa, Calif.). Sanger sequencing was performed on a 3700 Genetic Analyzer, following standard PCR, cleanup and cycle sequencing methods using Big Dye v.3.1 reagents (Applied Biosystems, Foster City, Calif.).

Using a DNA-based Ion Torrent™ (Life Technologies, South San Francisco, Calif.) sequencing assay to assess the entire coding region of DDR2 as well as exons 11 and 15 of BRAF, with confirmation by the Sanger sequencing method, we identified DDR2 missense point mutations in 12/269 (4.5%) cases of melanoma. The mutation frequency did not differ markedly by BRAF V600 mutation status in that DDR2 mutations were detected in 6/140 BRAF-mutated cases (V600E in 4, V600K in 2) and 7/129 without BRAF mutations. All but one of the DDR2-mutated melanomas were advanced stage: 3 were detected in extracutaneous metastases, and 7 in secondary skin or subcutaneous nodules, with no DDR2 mutations identified in 31 early stage primary cutaneous melanomas screened. Also, no DDR2 mutations were identified in 29 benign nevi, including blue nevi, typical dermal and compound nevi and dysplastic nevi.

In five cases, DDR2 mutations involved highly evolutionarily conserved residues in the kinase domain (e.g., F574C, S667F, and L701F shown in FIG. 2) suggesting hypofunctional effects on DDR2 kinase activity. Mutations in the four other cases were R458H, S467F, P476S and I488S, all located in the DDR2-specific region of the cytoplasmic domain. The clustering of mutations at highly conserved kinase domain residues in melanoma was different from previous findings in lung carcinomas, where mutations were more widely scattered and involved the discoidin and cytoplasmic domains and less conserved areas of the kinase domains.

DDR2 transcript levels were assessed from total RNA extracted from FFPE sections of macrodissected human melanoma samples, using one-step reverse transcription/cDNA synthesis and real-time PCR with Gene Expression assay primer/probe sets for the DDR1, DDR2 and GAPDH genes on the 7500 detection system (all Applied Biosystems). DDR2 transcript levels were normalized to GAPDH transcripts using the delta Ct method. Samples include advanced stage melanomas with DDR2 mutation (n=5), without DDR2 or BRAF V600 mutation (wt, n=17), and with BRAF V600 mutation but without DDR2 mutation (n=20).

Figure 3:
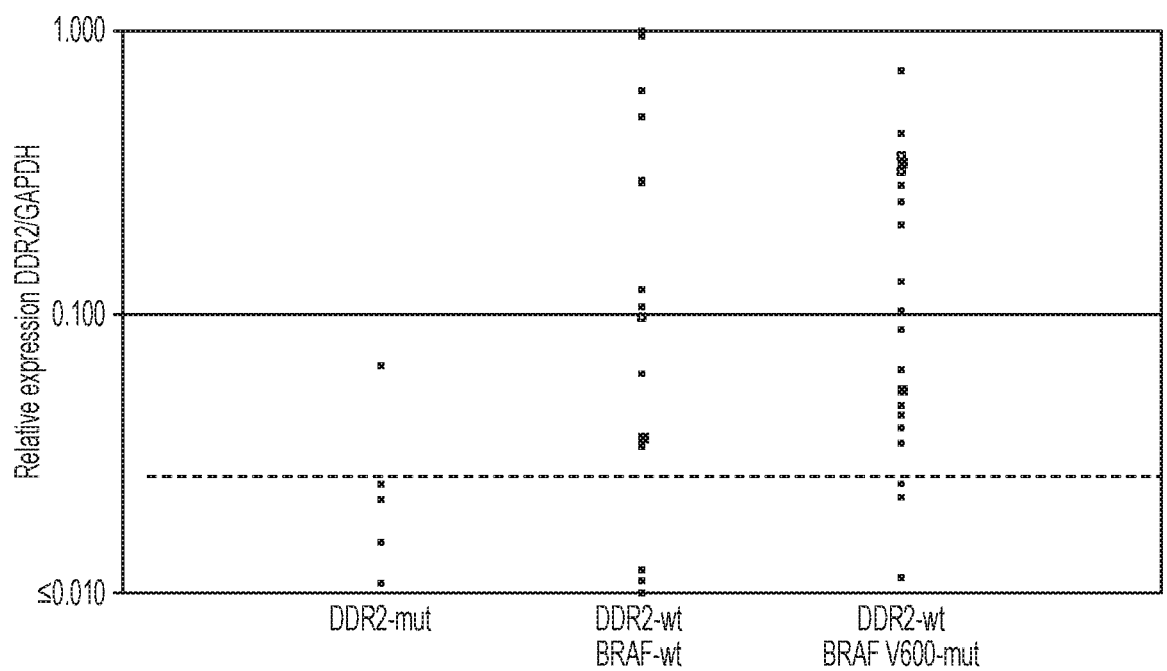
FIG. 3 shows DDR2 expressed at low levels in DDR2-mutated melanoma.

Using reverse-transcription PCR on macrodissected FFPE melanoma samples, we noted that DDR2 was underexpressed in 4 of the 5 DDR2-mutated melanomas with available material as compared to only a small minority of advanced stage DDR2/BRAF-unmutated melaomas or BRAF V600-mutated cases that lacked DDR2 mutations (FIG. 3). DDR2 mutations were seen in 4/10 cases with relative DDR2/GAPDH transcript levels below 0.025 compared to 1/32 cases with ratios above 0.025 ($p=0.008$). DDR1 transcript levels were more variable in the melanoma samples but also low in the DDR2-mutated subgroup (data not shown). This suggests that DDR2 expression can be used as a screening tool for DDR2 mutations.

Downregulation of DDR2 has also been noted in lung carcinoma, with upregulation observed in some other tumor types. In the DDR2-mutated melanomas identified here, decreased DDR2 activity could be produced by a combination of inactivating or hypofunctional mutations in one allele and transcriptional downregulation of the other allele.

DDR2 kinase domain mutations occur in a subset of BRAF-mutated advanced-stage melanomas and likely produce hypofunctional kinases based on the codons affected. In many cases, the DDR2-mutated overlaps with the BRAF-mutated group of typical sun-exposed melanomas but, unlike BRAF, DDR2 mutations have not yet been observed in nevi.

Example 5

Figure 4:
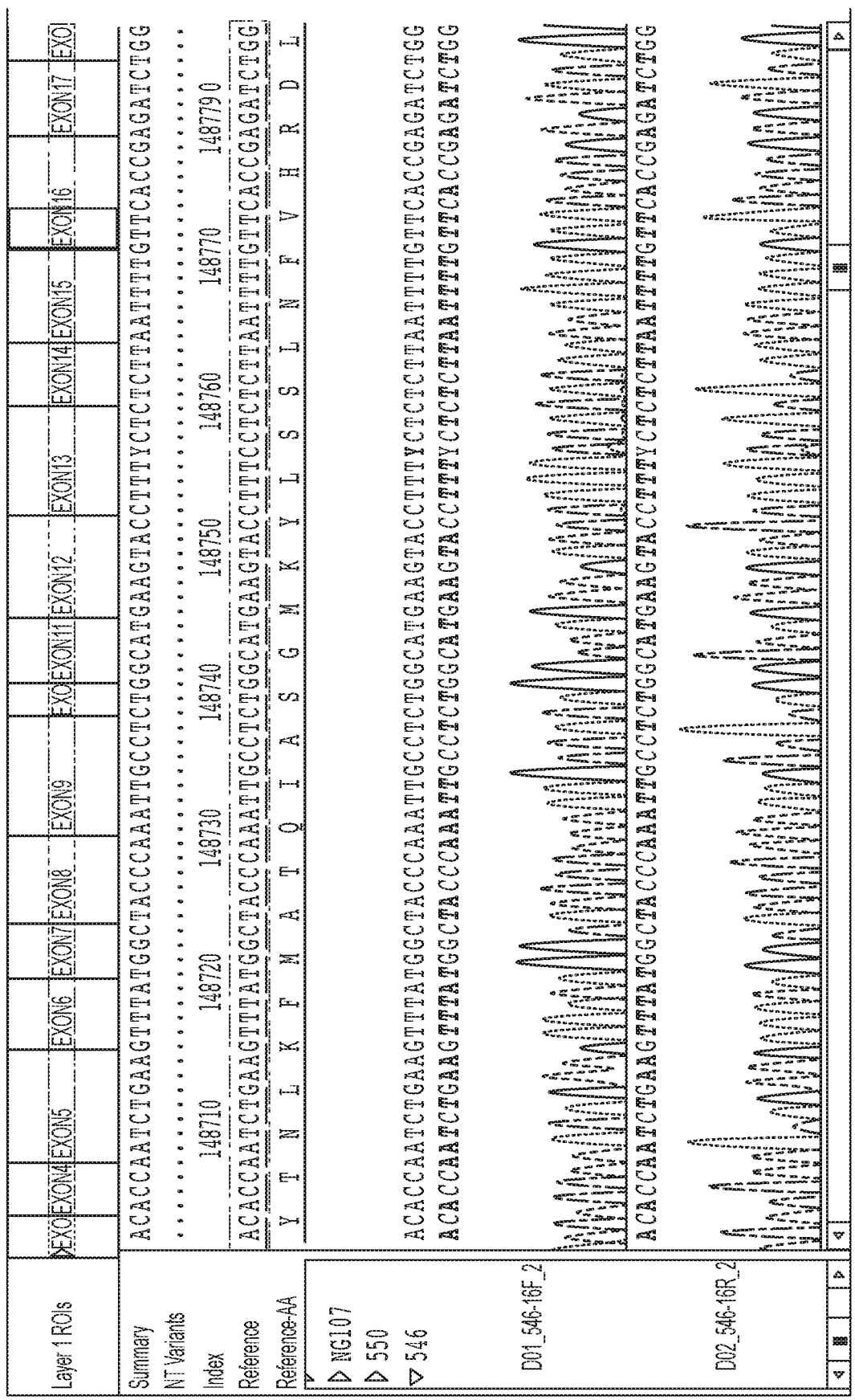
FIG. 4 shows an S702F kinase domain mutation in basal cell carcinoma.
Figure 5:
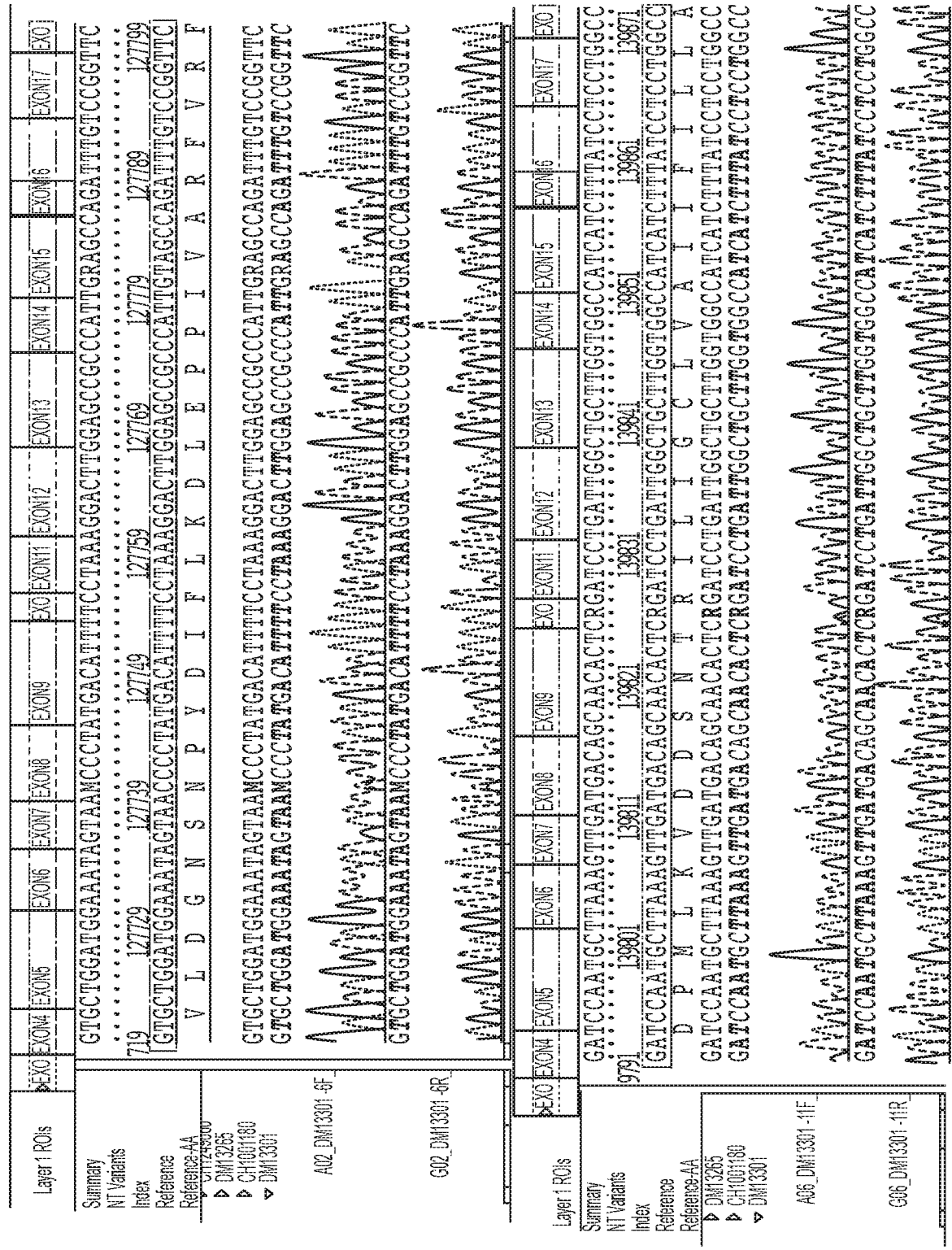
FIG. 5 shows N146K and R399Q biallelic DDR2 mutations in basal cell carcinoma.

Somatic DDR2 mutations were identified in basal cell carcinoma, including in the discoidin domain (N146K), the intracellular interacting domain (R399Q) and the kinase domain (S702F). See FIGS. 4 and 5. The frequency of DDR2 mutations in a small sampling of basal cell carcinomas was 32%.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Other embodiments are set forth within the following claims.

The invention claimed is:

1. A kit comprising oligonucleotide primer pairs suitable for amplifying multiple target segments of a DDR2 gene, wherein at least one primer of each oligonucleotide primer pair is detectably labeled, and wherein the kit comprises at least one primer selected from the group consisting of SEQ ID NOs: 1-50, wherein the at least one primer comprises a detectable marker, and wherein the detectable marker comprises a radioactive isotopes or a fluorescent marker.

2. The kit of claim 1, wherein the kit comprises primer pairs suitable for amplifying a full coding sequence of the DDR2 gene.

3. The kit of claim 1, further comprising an oligonucleotide primer pair suitable for amplifying BRAF exon 11 and/or exon 15.

4. The kit of claim 3, wherein the BRAF exon 11 primer pair comprises SEQ ID NO: 51 and/or SEQ ID NO: 52.

5. The kit of claim 3, wherein the BRAF exon 15 primer pair comprises SEQ ID NO: 53 and/or SEQ ID NO: 54.

6. The kit of claim 1, wherein the oligonucleotide primer pairs comprise peptide nucleic acid primers, locked nucleic acid primers, or phosphorothioate modified primers.

7. The kit of claim 1, wherein the kit is for use in detecting the presence of one or more mutations in a sample obtained from a human suspected of having melanoma or basal cell carcinoma (BCC).

* * * * *

SEQUENCE LISTING

```
<160> NUMBER OF SEQ ID NOS: 170

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tccagttcca acaccatctt c                                                21

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttctctttg gtttctcttg gtc                                              23
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cccaaccctc acctctcaag                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccagtggaac ctgatgacct                                              20

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccatgcagga ggtcatgg                                                18

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cactcattct cttctctctc ctca                                         24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccattgtagc cagatttgtc c                                            21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cttggctgtg tttcctttgc                                              20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctcttctcct ggcctgagc                                                19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cccagaccca tgaataccac                                               20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcacatgcct ctttctctac ca                                            22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagtgctact tccgctctga                                               20

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cccagtgctc ggtttgtc                                                 18

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gctctgactc acccttgttt t                                             21

-continued

```
<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccttctctcc ctggtcacag                                                 20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggatcctgat tggctgctt                                                  19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tctccttgct cttctcttcc a                                               21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
accgctcctc atcacctagt                                                 20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctcgttgccc ttgtcttcc                                                  19

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20 gaggggggtgc cccactat                                                  18

<210> SEQ ID NO 21
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agtgcctgcc gtcaccat                                                 18

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgatgctgag actagatgac ttttg                                         25

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gggaatggaa aaattcaaag a                                             21

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tttatctatg tctgtatcct cccaag                                        26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccatctatta gctgtgtgta tcactg                                        26

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccttctgtct tcttgtctat ttcctc                                        26

<210> SEQ ID NO 27
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tctcttaatt ttgttcaccg aga                                             23

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctttggaatg agcaggaacc                                                 20

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgatttccca ttcttttctt tactt                                           25

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tttgtgggag actttcacct tt                                              22

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tttcctttat ttttgttccc aaag                                            24

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gctgctggag aagagatacg a                                               21

<210> SEQ ID NO 33
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 33
tctgtttggc ttgacttgac tt                                           22

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gacgggactc gagtgatgat                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcgatcgtaa gtcgagttgg                                              20

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cccaccacat catcctcac                                               19

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgtgttgcct cctgtcactc                                              20

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tggggaactc ctccacag                                                18

<210> SEQ ID NO 39
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 39
aagggaatca agaatcaac tca                                           23

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gctcggagca ttttcaca                                                18

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggaaaattca aaatgtagac cacag                                        25

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
catgtattca gtgatcatac agagagg                                      27

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agaaggaaga cctggcttgt t                                            21

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tgtgtagttc ttaccacta aacagt                                        26

<210> SEQ ID NO 45
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 45
gccctggatc cggtaatagt                                              20

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cagggcttta aaatgctgag a                                            21

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tctgacagct gggaataggg                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccattcatcc ccaacagttc                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcagaaggtg gatttcttgg                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aggacctgag ccgtaggaac                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 51
tccaattctt tgtcccactg                                                 20

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tgtcacaatg tcaccacatt aca                                             23

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gacccactcc atcgagattt                                                 20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tcagtggaaa aatagcctca a                                               21

<210> SEQ ID NO 55
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tgtaaaacga cggccagttg agaattgtac tcattcatgt tgg                       43

<210> SEQ ID NO 56
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
caggaaacag ctatgaccgt agtccctctt ggcagctt                             38

<210> SEQ ID NO 57
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 57
tgtaaaacga cggccagttc ttattccttg ttcaatattc agtg                    44

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
caggaaacag ctatgacccc cctagggtca ggaatctg                           38

<210> SEQ ID NO 59
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgtaaaacga cggccagtca gctgcttgcc tgtgaac                            37

<210> SEQ ID NO 60
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
caggaaacag ctatgaccca cacagaaaac ctgtaccctt c                       41

<210> SEQ ID NO 61
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgtaaaacga cggccagtgt ggtggggtga agaaaagt                           38

<210> SEQ ID NO 62
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
caggaaacag ctatgacctc cctttctgat ttgattgc                           38

<210> SEQ ID NO 63
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 63
tgtaaaacga cggccagtcg ctgtgcaagc ttataccc                              38

<210> SEQ ID NO 64
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
caggaaacag ctatgacctt gattgattat tgatcccaag a                          41

<210> SEQ ID NO 65
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tgtaaaacga cggccagtga gtgaagatgc cgggtaaa                              38

<210> SEQ ID NO 66
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
caggaaacag ctatgacctg aactggcatc agcctaga                              38

<210> SEQ ID NO 67
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tgtaaaacga cggccagtta ctgagttggc tggcactg                              38

<210> SEQ ID NO 68
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
caggaaacag ctatgacctg agaagttctg ggcatgtg                              38

<210> SEQ ID NO 69
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
```
tgtaaaacga cggccagttc actaaattga tcttgtaatg tgc                          43

<210> SEQ ID NO 70
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
caggaaacag ctatgacccc agggctactc ttcatcca                                38

<210> SEQ ID NO 71
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tgtaaaacga cggccagtag gaacagggtc tacctcca                                38

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
caggaaacag ctatgaccaa atgtttgcaa tttgcctttt                              40

<210> SEQ ID NO 73
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tgtaaaacga cggccagttg ggagagctga gtttaagaag a                            41

<210> SEQ ID NO 74
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
caggaaacag ctatgaccgc agagactaaa aatagatgca atga                         44

<210> SEQ ID NO 75
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75

```
tgtaaaacga cggccagtgc cctcctctca gagttcct                             38
```

<210> SEQ ID NO 76
<211> LENGTH: 38
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 76

```
caggaaacag ctatgaccgt gaatccacct ctggaagg                             38
```

<210> SEQ ID NO 77
<211> LENGTH: 38
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 77

```
tgtaaaacga cggccagtgg aaatgcccag caagagta                             38
```

<210> SEQ ID NO 78
<211> LENGTH: 38
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 78

```
caggaaacag ctatgaccgc tcactgacct tcccatct                             38
```

<210> SEQ ID NO 79
<211> LENGTH: 38
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 79

```
tgtaaaacga cggccagtat aggccttggt gtgcattc                             38
```

<210> SEQ ID NO 80
<211> LENGTH: 37
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 80

```
caggaaacag ctatgaccac tgacttcccc caccatc                              37
```

<210> SEQ ID NO 81
<211> LENGTH: 40
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 81

```
tgtaaaacga cggccagtga atgttgagct ttcaaccta                            40
```

<210> SEQ ID NO 82
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
caggaaacag ctatgaccag cccacaagcc agttgtta                           38

<210> SEQ ID NO 83
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tgtaaaacga cggccagtag aattccttgc ctgtggtg                           38

<210> SEQ ID NO 84
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
caggaaacag ctatgaccag tgacaaagac taacacctgg a                       41

<210> SEQ ID NO 85
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tgtaaaacga cggccagtca aatcaaacca tgatgcaaa                          39

<210> SEQ ID NO 86
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
caggaaacag ctatgacctg tccagatgga gtggcata                           38

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tgtaaaacga cggccagt                                                 18

```
<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
caggaaacag ctatgacc                                                   18

<210> SEQ ID NO 89
<211> LENGTH: 830
<212> TYPE: PRT
<213> ORGANISM: Unknown
<220> FEATURE:
<223> OTHER INFORMATION: Description of Unknown:
      DDR2 polypeptide

<400> SEQUENCE: 89
```

Lys Ala Gln Val Asn Pro Ala Ile Cys Arg Tyr Pro Leu Gly Met Ser
1               5                   10                  15

Gly Gly Gln Ile Pro Asp Glu Asp Ile Thr Ala Ser Ser Gln Trp Ser
            20                  25                  30

Glu Ser Thr Ala Ala Lys Tyr Gly Arg Leu Asp Ser Glu Glu Gly Asp
        35                  40                  45

Gly Ala Trp Cys Pro Glu Ile Pro Val Glu Pro Asp Asp Leu Lys Glu
    50                  55                  60

Phe Leu Gln Ile Asp Leu His Thr Leu His Phe Ile Thr Leu Val Gly
65                  70                  75                  80

Thr Gln Gly Arg His Ala Gly Gly His Gly Ile Glu Phe Ala Pro Met
                85                  90                  95

Tyr Lys Ile Asn Tyr Ser Arg Asp Gly Thr Arg Trp Ile Ser Trp Arg
            100                 105                 110

Asn Arg His Gly Lys Gln Val Leu Asp Gly Asn Ser Asn Pro Tyr Asp
        115                 120                 125

Ile Phe Leu Lys Asp Leu Glu Pro Pro Ile Val Ala Arg Phe Val Arg
    130                 135                 140

Phe Ile Pro Val Thr Asp His Ser Met Asn Val Cys Met Arg Val Glu
145                 150                 155                 160

Leu Tyr Gly Cys Val Trp Leu Asp Gly Leu Val Ser Tyr Asn Ala Pro
                165                 170                 175

Ala Gly Gln Gln Phe Val Leu Pro Gly Gly Ser Ile Ile Tyr Leu Asn
            180                 185                 190

Asp Ser Val Tyr Asp Gly Ala Val Gly Tyr Ser Met Thr Glu Gly Leu
        195                 200                 205

Gly Gln Leu Thr Asp Gly Val Ser Gly Leu Asp Asp Phe Thr Gln Thr
    210                 215                 220

His Glu Tyr His Val Trp Pro Gly Tyr Asp Tyr Val Gly Trp Arg Asn
225                 230                 235                 240

Glu Ser Ala Thr Asn Gly Tyr Ile Glu Ile Met Phe Glu Phe Asp Arg
                245                 250                 255

Ile Arg Asn Phe Thr Thr Met Lys Val His Cys Asn Asn Met Phe Ala
            260                 265                 270

Lys Gly Val Lys Ile Phe Lys Glu Val Gln Cys Tyr Phe Arg Ser Glu
        275                 280                 285

Ala Ser Glu Trp Glu Pro Asn Ala Ile Ser Phe Pro Leu Val Leu Asp

```
                290                 295                 300
Asp Val Asn Pro Ser Ala Arg Phe Val Thr Val Pro Leu His His Arg
305                 310                 315                 320

Met Ala Ser Ala Ile Lys Cys Gln Tyr His Phe Ala Asp Thr Trp Met
                325                 330                 335

Met Phe Ser Glu Ile Thr Phe Gln Ser Asp Ala Ala Met Tyr Asn Asn
                340                 345                 350

Ser Glu Ala Leu Pro Thr Ser Pro Met Ala Pro Thr Thr Tyr Asp Pro
                355                 360                 365

Met Leu Lys Val Asp Asp Ser Asn Thr Arg Ile Leu Ile Gly Cys Leu
                370                 375                 380

Val Ala Ile Ile Phe Ile Leu Leu Ala Ile Ile Val Ile Ile Leu Trp
385                 390                 395                 400

Arg Gln Phe Trp Gln Lys Met Leu Glu Lys Ala Ser Arg Arg Met Leu
                405                 410                 415

Asp Asp Glu Met Thr Val Ser Leu Ser Leu Pro Ser Asp Ser Ser Met
                420                 425                 430

Phe Asn Asn Asn Arg Ser Ser Ser Pro Ser Glu Gln Gly Ser Asn Ser
                435                 440                 445

Thr Tyr Asp Arg Ile Phe Pro Leu Arg Pro Asp Tyr Gln Glu Pro Ser
                450                 455                 460

Arg Leu Ile Arg Lys Leu Pro Glu Phe Ala Pro Gly Glu Glu Glu Ser
465                 470                 475                 480

Gly Cys Ser Gly Val Val Lys Pro Val Gln Pro Ser Gly Pro Glu Gly
                485                 490                 495

Val Pro His Tyr Ala Glu Ala Asp Ile Val Asn Leu Gln Gly Val Thr
                500                 505                 510

Gly Gly Asn Thr Tyr Ser Val Pro Ala Val Thr Met Asp Leu Leu Ser
                515                 520                 525

Gly Lys Asp Val Ala Val Glu Glu Phe Pro Arg Lys Leu Leu Thr Phe
                530                 535                 540

Lys Glu Lys Leu Gly Glu Gly Gln Phe Gly Glu Val His Leu Cys Glu
545                 550                 555                 560

Val Glu Gly Met Glu Lys Phe Lys Asp Lys Asp Phe Ala Leu Asp Val
                565                 570                 575

Ser Ala Asn Gln Pro Val Leu Val Ala Val Lys Met Leu Arg Ala Asp
                580                 585                 590

Ala Asn Lys Asn Ala Arg Asn Asp Phe Leu Lys Glu Ile Lys Ile Met
                595                 600                 605

Ser Arg Leu Lys Asp Pro Asn Ile Ile His Leu Leu Ser Val Cys Ile
                610                 615                 620

Thr Asp Asp Pro Leu Cys Met Ile Thr Glu Tyr Met Glu Asn Gly Asp
625                 630                 635                 640

Leu Asn Gln Phe Leu Ser Arg His Glu Pro Pro Asn Ser Ser Ser Ser
                645                 650                 655

Asp Val Arg Thr Val Ser Tyr Thr Asn Leu Lys Phe Met Ala Thr Gln
                660                 665                 670

Ile Ala Ser Gly Met Lys Tyr Leu Ser Ser Leu Asn Phe Val His Arg
                675                 680                 685

Asp Leu Ala Thr Arg Asn Cys Leu Val Gly Asn Tyr Thr Ile Lys
                690                 695                 700

Ile Ala Asp Phe Gly Met Ser Arg Asn Leu Tyr Ser Gly Asp Tyr Tyr
705                 710                 715                 720
```

-continued

```
Arg Ile Gln Gly Arg Ala Val Leu Pro Ile Arg Trp Met Ser Trp Glu
                725                 730                 735

Ser Ile Leu Leu Gly Lys Phe Thr Thr Ala Ser Asp Val Trp Ala Phe
            740                 745                 750

Gly Val Thr Leu Trp Glu Thr Phe Thr Phe Cys Gln Glu Gln Pro Tyr
        755                 760                 765

Ser Gln Leu Ser Asp Glu Gln Val Ile Glu Asn Thr Gly Glu Phe Phe
    770                 775                 780

Arg Asp Gln Gly Arg Gln Thr Tyr Leu Pro Gln Pro Ala Ile Cys Pro
785                 790                 795                 800

Asp Ser Val Tyr Lys Leu Met Leu Ser Cys Trp Arg Arg Asp Thr Lys
                805                 810                 815

Asn Arg Pro Ser Phe Gln Glu Ile His Leu Leu Leu Gln
            820                 825                 830

<210> SEQ ID NO 90
<211> LENGTH: 847
<212> TYPE: PRT
<213> ORGANISM: Unknown
<220> FEATURE:
<223> OTHER INFORMATION: Description of Unknown:
      DDR1 polypeptide

<400> SEQUENCE: 90

Lys Gly His Phe Asp Pro Ala Lys Cys Arg Tyr Ala Leu Gly Met Gln
1               5                   10                  15

Asp Arg Thr Ile Pro Asp Ser Asp Ile Ser Ala Ser Ser Ser Trp Ser
            20                  25                  30

Asp Ser Thr Ala Ala Arg His Ser Arg Leu Glu Ser Ser Asp Gly Asp
        35                  40                  45

Gly Ala Trp Cys Pro Ala Gly Ser Val Phe Pro Lys Glu Glu Glu Tyr
    50                  55                  60

Leu Gln Val Asp Leu Gln Arg Leu His Leu Val Ala Leu Val Gly Thr
65                  70                  75                  80

Gln Gly Arg His Ala Gly Gly Leu Gly Lys Glu Phe Ser Arg Ser Tyr
                85                  90                  95

Arg Leu Arg Tyr Ser Arg Asp Gly Arg Arg Trp Met Gly Trp Lys Asp
            100                 105                 110

Arg Trp Gly Gln Glu Val Ile Ser Gly Asn Glu Asp Pro Glu Gly Val
        115                 120                 125

Val Leu Lys Asp Leu Gly Pro Pro Met Val Ala Arg Leu Val Arg Phe
    130                 135                 140

Tyr Pro Arg Ala Asp Arg Val Met Ser Val Cys Leu Arg Val Glu Leu
145                 150                 155                 160

Tyr Gly Cys Leu Trp Arg Asp Gly Leu Leu Ser Tyr Thr Ala Pro Val
                165                 170                 175

Gly Gln Thr Met Tyr Leu Ser Glu Ala Val Tyr Leu Asn Asp Ser Thr
            180                 185                 190

Tyr Asp Gly His Thr Val Gly Gly Leu Gln Tyr Gly Gly Leu Gly Gln
        195                 200                 205

Leu Ala Asp Gly Val Val Gly Leu Asp Asp Phe Arg Lys Ser Gln Glu
    210                 215                 220

Leu Arg Val Trp Pro Gly Tyr Asp Tyr Val Gly Trp Ser Asn His Ser
225                 230                 235                 240

Phe Ser Ser Gly Tyr Val Glu Met Glu Phe Glu Phe Asp Arg Leu Arg
```

```
                    245                 250                 255
Ala Phe Gln Ala Met Gln Val His Cys Asn Asn Met His Thr Leu Gly
                260                 265                 270

Ala Arg Leu Pro Gly Gly Val Glu Cys Arg Phe Arg Arg Gly Pro Ala
            275                 280                 285

Met Ala Trp Glu Gly Glu Pro Met Arg His Asn Leu Gly Gly Asn Leu
        290                 295                 300

Gly Asp Pro Arg Ala Arg Ala Val Ser Val Pro Leu Gly Gly Arg Val
305                 310                 315                 320

Ala Arg Phe Leu Gln Cys Arg Phe Leu Phe Ala Gly Pro Trp Leu Leu
                325                 330                 335

Phe Ser Glu Ile Ser Phe Ile Ser Asp Val Val Asn Ser Ser Pro
                340                 345                 350

Ala Leu Gly Gly Thr Phe Pro Pro Ala Pro Trp Trp Pro Gly Pro
            355                 360                 365

Pro Pro Thr Asn Phe Ser Ser Leu Glu Leu Glu Pro Arg Gly Gln Gln
        370                 375                 380

Pro Val Ala Lys Ala Glu Gly Ser Pro Thr Ala Ile Leu Ile Gly Cys
385                 390                 395                 400

Leu Val Ala Ile Ile Leu Leu Leu Leu Ile Ile Ala Leu Met Leu
                405                 410                 415

Trp Arg Leu His Trp Arg Arg Leu Leu Ser Ala Glu Arg Arg Val Leu
                420                 425                 430

Glu Glu Glu Leu Thr Val His Leu Ser Val Pro Gly Asp Thr Ile Leu
            435                 440                 445

Ile Asn Asn Arg Pro Gly Pro Arg Glu Pro Pro Tyr Gln Glu Pro
450                 455                 460

Arg Pro Arg Gly Asn Pro Pro His Ser Ala Pro Cys Val Pro Asn Gly
465                 470                 475                 480

Ser Ala Tyr Ser Gly Asp Tyr Met Glu Pro Glu Lys Pro Gly Ala Pro
            485                 490                 495

Leu Leu Pro Pro Pro Gln Asn Ser Val Pro His Tyr Ala Glu Ala
            500                 505                 510

Asp Ile Val Thr Leu Gln Gly Val Thr Gly Gly Asn Thr Tyr Ala Val
        515                 520                 525

Pro Ala Leu Pro Pro Gly Ala Val Gly Asp Gly Pro Pro Arg Val Asp
530                 535                 540

Phe Pro Arg Ser Arg Leu Arg Phe Lys Glu Lys Leu Gly Glu Gly Gln
545                 550                 555                 560

Phe Gly Glu Val His Leu Cys Glu Val Asp Ser Pro Gln Asp Leu Val
                565                 570                 575

Ser Leu Asp Phe Pro Leu Asn Val Arg Lys Gly His Pro Leu Leu Val
            580                 585                 590

Ala Val Lys Ile Leu Arg Pro Asp Ala Thr Lys Asn Ala Arg Asn Asp
        595                 600                 605

Phe Leu Lys Glu Val Lys Ile Met Ser Arg Leu Lys Asp Pro Asn Ile
    610                 615                 620

Ile Arg Leu Leu Gly Val Cys Val Gln Asp Asp Pro Leu Cys Met Ile
625                 630                 635                 640

Thr Asp Tyr Met Glu Asn Gly Asp Leu Asn Gln Phe Leu Ser Ala His
            645                 650                 655

Gln Leu Glu Asp Lys Ala Ala Glu Gly Ala Pro Gly Asp Gly Gln Ala
            660                 665                 670
```

```
Ala Gln Gly Pro Thr Ile Ser Tyr Pro Met Leu Leu His Val Ala Ala
            675                 680                 685

Gln Ile Ala Ser Gly Met Arg Tyr Leu Ala Thr Leu Asn Phe Val His
        690                 695                 700

Arg Asp Leu Ala Thr Arg Asn Cys Leu Val Gly Glu Asn Phe Thr Ile
705                 710                 715                 720

Lys Ile Ala Asp Phe Gly Met Ser Arg Asn Leu Tyr Ala Gly Asp Tyr
                725                 730                 735

Tyr Arg Val Gln Gly Arg Ala Val Leu Pro Ile Arg Trp Met Ala Trp
            740                 745                 750

Glu Cys Ile Leu Met Gly Lys Phe Thr Thr Ala Ser Asp Val Trp Ala
            755                 760                 765

Phe Gly Val Thr Leu Trp Glu Val Leu Met Leu Cys Arg Ala Gln Pro
        770                 775                 780

Phe Gly Gln Leu Thr Asp Glu Gln Val Ile Glu Asn Ala Gly Glu Phe
785                 790                 795                 800

Phe Arg Asp Gln Gly Arg Gln Val Tyr Leu Ser Arg Pro Pro Ala Cys
                805                 810                 815

Pro Gln Gly Leu Tyr Glu Leu Met Leu Arg Cys Trp Ser Arg Glu Ser
            820                 825                 830

Glu Gln Arg Pro Pro Phe Ser Gln Leu His Arg Phe Leu Ala Glu
        835                 840                 845

<210> SEQ ID NO 91
<211> LENGTH: 20
<212> TYPE: DNA
<213> ORGANISM: Unknown
<220> FEATURE:
<223> OTHER INFORMATION: Description of Unknown:
      DDR2 oligonucleotide

<400> SEQUENCE: 91
tgggagaagg acagtttggg                                               20

<210> SEQ ID NO 92
<211> LENGTH: 20
<212> TYPE: DNA
<213> ORGANISM: Unknown
<220> FEATURE:
<223> OTHER INFORMATION: Description of Unknown:
      DDR2 oligonucleotide

<400> SEQUENCE: 92
tgggagaagg acagtktggg                                               20

<210> SEQ ID NO 93
<211> LENGTH: 20
<212> TYPE: DNA
<213> ORGANISM: Unknown
<220> FEATURE:
<223> OTHER INFORMATION: Description of Unknown:
      DDR2 oligonucleotide

<400> SEQUENCE: 93
tgggagaagg acagtgtggg                                               20

<210> SEQ ID NO 94
<211> LENGTH: 20
<212> TYPE: DNA
<213> ORGANISM: Unknown
<220> FEATURE:
```

```
<223> OTHER INFORMATION: Description of Unknown:
      DDR2 oligonucleotide

<400> SEQUENCE: 94
tgggagaagg acattttggg                                               20

<210> SEQ ID NO 95
<211> LENGTH: 20
<212> TYPE: DNA
<213> ORGANISM: Unknown
<220> FEATURE:
<223> OTHER INFORMATION: Description of Unknown:
      DDR2 oligonucleotide

<400> SEQUENCE: 95
tgggagaggg acagtttggg                                               20

<210> SEQ ID NO 96
<211> LENGTH: 20
<212> TYPE: DNA
<213> ORGANISM: Unknown
<220> FEATURE:
<223> OTHER INFORMATION: Description of Unknown:
      DDR2 oligonucleotide

<400> SEQUENCE: 96
tgggagaggg acaagttggg                                               20

<210> SEQ ID NO 97
<211> LENGTH: 7
<212> TYPE: PRT
<213> ORGANISM: Unknown
<220> FEATURE:
<223> OTHER INFORMATION: Description of Unknown:
      DDR2 peptide

<400> SEQUENCE: 97

Leu Gly Glu Gly Gln Phe Gly
1               5

<210> SEQ ID NO 98
<211> LENGTH: 21
<212> TYPE: DNA
<213> ORGANISM: Unknown
<220> FEATURE:
<223> OTHER INFORMATION: Description of Unknown:
      DDR2 oligonucleotide

<400> SEQUENCE: 98
tgggagaagg acagtktggg g                                             21

<210> SEQ ID NO 99
<211> LENGTH: 23
<212> TYPE: PRT
<213> ORGANISM: Unknown
<220> FEATURE:
<223> OTHER INFORMATION: Description of Unknown:
      DDR2 peptide

<400> SEQUENCE: 99

Phe Lys Glu Lys Leu Gly Glu Gly Gln Phe Gly Glu Val His Leu Cys
1               5                   10                  15

Glu Val Glu Gly Met Glu Lys
            20

<210> SEQ ID NO 100
```

```
<211> LENGTH: 21
<212> TYPE: PRT
<213> ORGANISM: Unknown
<220> FEATURE:
<223> OTHER INFORMATION: Description of Unknown:
      BRAF peptide

<400> SEQUENCE: 100

Val Gly Gln Arg Ile Gly Ser Gly Ser Phe Gly Thr Val Tyr Lys Gly
1               5                   10                  15

Lys Trp His Gly Asp
            20

<210> SEQ ID NO 101
<211> LENGTH: 23
<212> TYPE: PRT
<213> ORGANISM: Unknown
<220> FEATURE:
<223> OTHER INFORMATION: Description of Unknown:
      EGFR peptide

<400> SEQUENCE: 101

Lys Ile Lys Val Leu Gly Ser Gly Ala Phe Gly Thr Val Tyr Lys Gly
1               5                   10                  15

Leu Trp Ile Pro Glu Gly Glu
            20

<210> SEQ ID NO 102
<211> LENGTH: 23
<212> TYPE: PRT
<213> ORGANISM: Unknown
<220> FEATURE:
<223> OTHER INFORMATION: Description of Unknown:
      ERBB2 peptide

<400> SEQUENCE: 102

Lys Val Lys Val Leu Gly Ser Gly Ala Phe Gly Thr Val Tyr Lys Gly
1               5                   10                  15

Ile Trp Ile Pro Asp Gly Glu
            20

<210> SEQ ID NO 103
<211> LENGTH: 19
<212> TYPE: PRT
<213> ORGANISM: Unknown
<220> FEATURE:
<223> OTHER INFORMATION: Description of Unknown:
      ABL1 peptide

<400> SEQUENCE: 103

Met Lys His Lys Leu Gly Gly Gly Gln Tyr Gly Glu Val Tyr Glu Gly
1               5                   10                  15

Val Trp Lys

<210> SEQ ID NO 104
<211> LENGTH: 23
<212> TYPE: PRT
<213> ORGANISM: Unknown
<220> FEATURE:
<223> OTHER INFORMATION: Description of Unknown:
      ALK peptide

<400> SEQUENCE: 104

Leu Ile Arg Gly Leu Gly His Gly Ala Phe Gly Glu Val Tyr Glu Gly
1               5                   10                  15
```

Gln Val Ser Gly Met Pro Asn
            20

<210> SEQ ID NO 105
<211> LENGTH: 23
<212> TYPE: PRT
<213> ORGANISM: Unknown
<220> FEATURE:
<223> OTHER INFORMATION: Description of Unknown:
      AKT1 peptide

<400> SEQUENCE: 105

Tyr Leu Lys Leu Leu Gly Lys Gly Thr Phe Gly Lys Val Ile Leu Val
1               5                   10                  15

Lys Glu Lys Ala Thr Gly Arg
            20

<210> SEQ ID NO 106
<211> LENGTH: 23
<212> TYPE: PRT
<213> ORGANISM: Unknown
<220> FEATURE:
<223> OTHER INFORMATION: Description of Unknown:
      MET peptide

<400> SEQUENCE: 106

Phe Asn Glu Val Ile Gly Arg Gly His Phe Gly Cys Val Tyr His Gly
1               5                   10                  15

Thr Leu Leu Asp Asn Asp Gly
            20

<210> SEQ ID NO 107
<211> LENGTH: 23
<212> TYPE: PRT
<213> ORGANISM: Unknown
<220> FEATURE:
<223> OTHER INFORMATION: Description of Unknown:
      FGFR1 peptide

<400> SEQUENCE: 107

Leu Gly Lys Pro Leu Gly Glu Gly Cys Phe Gly Gln Val Val Leu Ala
1               5                   10                  15

Glu Ala Ile Gly Leu Asp Lys
            20

<210> SEQ ID NO 108
<211> LENGTH: 23
<212> TYPE: PRT
<213> ORGANISM: Unknown
<220> FEATURE:
<223> OTHER INFORMATION: Description of Unknown:
      FGFR2 peptide

<400> SEQUENCE: 108

Leu Gly Lys Pro Leu Gly Glu Gly Cys Phe Gly Gln Val Val Leu Ala
1               5                   10                  15

Glu Ala Ile Gly Ile Asp Lys
            20

<210> SEQ ID NO 109
<211> LENGTH: 23
<212> TYPE: PRT
<213> ORGANISM: Unknown
<220> FEATURE:
<223> OTHER INFORMATION: Description of Unknown:
      FGFR3 peptide

```
<400> SEQUENCE: 109

Leu Gly Lys Pro Leu Gly Glu Gly Cys Phe Gly Gln Val Val Leu Ala
1               5                   10                  15

Glu Ala Ile Gly Ile Asp Lys
            20

<210> SEQ ID NO 110
<211> LENGTH: 23
<212> TYPE: PRT
<213> ORGANISM: Unknown
<220> FEATURE:
<223> OTHER INFORMATION: Description of Unknown:
      FLT3 peptide

<400> SEQUENCE: 110

Phe Gly Lys Val Leu Gly Ser Gly Ala Phe Gly Lys Val Met Asn Ala
1               5                   10                  15

Thr Ala Tyr Gly Ile Ser Lys
            20

<210> SEQ ID NO 111
<211> LENGTH: 23
<212> TYPE: PRT
<213> ORGANISM: Unknown
<220> FEATURE:
<223> OTHER INFORMATION: Description of Unknown:
      PDGFRA peptide

<400> SEQUENCE: 111

Leu Gly Arg Val Leu Gly Ser Gly Ala Phe Gly Lys Val Val Glu Gly
1               5                   10                  15

Thr Ala Tyr Gly Leu Ser Arg
            20

<210> SEQ ID NO 112
<211> LENGTH: 23
<212> TYPE: PRT
<213> ORGANISM: Unknown
<220> FEATURE:
<223> OTHER INFORMATION: Description of Unknown:
      ERBB3 peptide

<400> SEQUENCE: 112

Lys Leu Lys Val Leu Gly Ser Gly Val Phe Gly Thr Val His Lys Gly
1               5                   10                  15

Val Trp Ile Pro Glu Gly Glu
            20

<210> SEQ ID NO 113
<211> LENGTH: 23
<212> TYPE: PRT
<213> ORGANISM: Unknown
<220> FEATURE:
<223> OTHER INFORMATION: Description of Unknown:
      ERBB4 peptide

<400> SEQUENCE: 113

Arg Val Lys Val Leu Gly Ser Gly Ala Phe Gly Thr Val Tyr Lys Gly
1               5                   10                  15

Ile Trp Val Pro Glu Gly Glu
            20

<210> SEQ ID NO 114
```

```
<211> LENGTH: 23
<212> TYPE: PRT
<213> ORGANISM: Unknown
<220> FEATURE:
<223> OTHER INFORMATION: Description of Unknown:
      JAK2 peptide

<400> SEQUENCE: 114

Phe Leu Gln Gln Leu Gly Lys Gly Asn Phe Gly Ser Val Glu Met Cys
1               5                   10                  15

Arg Tyr Asp Pro Leu Gln Asp
            20

<210> SEQ ID NO 115
<211> LENGTH: 23
<212> TYPE: PRT
<213> ORGANISM: Unknown
<220> FEATURE:
<223> OTHER INFORMATION: Description of Unknown:
      ROS1 peptide

<400> SEQUENCE: 115

Leu Arg Leu Leu Leu Gly Ser Gly Ala Phe Gly Glu Val Tyr Glu Gly
1               5                   10                  15

Thr Ala Val Asp Ile Leu Gly
            20

<210> SEQ ID NO 116
<211> LENGTH: 22
<212> TYPE: DNA
<213> ORGANISM: Unknown
<220> FEATURE:
<223> OTHER INFORMATION: Description of Unknown:
      DDR2 oligonucleotide

<400> SEQUENCE: 116
tcagtttctt tcccgccacg ag                                          22

<210> SEQ ID NO 117
<211> LENGTH: 22
<212> TYPE: DNA
<213> ORGANISM: Unknown
<220> FEATURE:
<223> OTHER INFORMATION: Description of Unknown:
      DDR2 oligonucleotide

<400> SEQUENCE: 117
tcagtttctt tyccgccacg ag                                          22

<210> SEQ ID NO 118
<211> LENGTH: 22
<212> TYPE: DNA
<213> ORGANISM: Unknown
<220> FEATURE:
<223> OTHER INFORMATION: Description of Unknown:
      DDR2 oligonucleotide

<400> SEQUENCE: 118
tcagtttctt ttccgccacg ag                                          22

<210> SEQ ID NO 119
<211> LENGTH: 22
<212> TYPE: DNA
<213> ORGANISM: Unknown
<220> FEATURE:
<223> OTHER INFORMATION: Description of Unknown:
      DDR2 oligonucleotide
```

```
<400> SEQUENCE: 119 tcagttttt tcccgccacg ag                                              22

<210> SEQ ID NO 120
<211> LENGTH: 8
<212> TYPE: PRT
<213> ORGANISM: Unknown
<220> FEATURE:
<223> OTHER INFORMATION: Description of Unknown:
      DDR2 peptide

<400> SEQUENCE: 120

Asn Gln Phe Leu Ser Arg His Glu
1               5

<210> SEQ ID NO 121
<211> LENGTH: 17
<212> TYPE: PRT
<213> ORGANISM: Unknown
<220> FEATURE:
<223> OTHER INFORMATION: Description of Unknown:
      DDR2 peptide

<400> SEQUENCE: 121

Tyr Met Glu Asn Gly Asp Leu Asn Gln Phe Leu Ser Arg His Glu Pro
1               5                   10                  15

Pro

<210> SEQ ID NO 122
<211> LENGTH: 17
<212> TYPE: PRT
<213> ORGANISM: Unknown
<220> FEATURE:
<223> OTHER INFORMATION: Description of Unknown:
      BRAF peptide

<400> SEQUENCE: 122

Trp Cys Lys Gly Ser Ser Leu Tyr His His Leu His Ile Ile Glu Thr
1               5                   10                  15

Lys

<210> SEQ ID NO 123
<211> LENGTH: 17
<212> TYPE: PRT
<213> ORGANISM: Unknown
<220> FEATURE:
<223> OTHER INFORMATION: Description of Unknown:
      EGFR peptide

<400> SEQUENCE: 123

Leu Met Pro Phe Gly Cys Leu Leu Asp Tyr Val Arg Glu His Lys Asp
1               5                   10                  15

Asn

<210> SEQ ID NO 124
<211> LENGTH: 17
<212> TYPE: PRT
<213> ORGANISM: Unknown
<220> FEATURE:
<223> OTHER INFORMATION: Description of Unknown:
      ERBB2 peptide

<400> SEQUENCE: 124

Leu Met Pro Tyr Gly Cys Leu Leu Asp His Val Arg Glu Asn Arg Gly
```

-continued

```
1               5                   10                  15
Arg

<210> SEQ ID NO 125
<211> LENGTH: 16
<212> TYPE: PRT
<213> ORGANISM: Unknown
<220> FEATURE:
<223> OTHER INFORMATION: Description of Unknown:
      ABL1 peptide

<400> SEQUENCE: 125

Phe Asn Thr Tyr Gly Asn Leu Leu Asp Tyr Leu Arg Glu Cys Asn Arg
1               5                   10                  15

<210> SEQ ID NO 126
<211> LENGTH: 17
<212> TYPE: PRT
<213> ORGANISM: Unknown
<220> FEATURE:
<223> OTHER INFORMATION: Description of Unknown:
      ALK peptide

<400> SEQUENCE: 126

Leu Met Ala Gly Gly Asp Leu Lys Ser Phe Leu Arg Glu Thr Arg Pro
1               5                   10                  15

Arg

<210> SEQ ID NO 127
<211> LENGTH: 16
<212> TYPE: PRT
<213> ORGANISM: Unknown
<220> FEATURE:
<223> OTHER INFORMATION: Description of Unknown:
      AKT1 peptide

<400> SEQUENCE: 127

Tyr Ala Asn Gly Gly Glu Leu Phe Phe His Leu Ser Arg Glu Arg Val
1               5                   10                  15

<210> SEQ ID NO 128
<211> LENGTH: 17
<212> TYPE: PRT
<213> ORGANISM: Unknown
<220> FEATURE:
<223> OTHER INFORMATION: Description of Unknown:
      MET peptide

<400> SEQUENCE: 128

Tyr Met Lys His Gly Asp Leu Arg Asn Phe Ile Arg Asn Glu Thr His
1               5                   10                  15

Asn

<210> SEQ ID NO 129
<211> LENGTH: 17
<212> TYPE: PRT
<213> ORGANISM: Unknown
<220> FEATURE:
<223> OTHER INFORMATION: Description of Unknown:
      FGFR1 peptide

<400> SEQUENCE: 129

Tyr Ala Ser Lys Gly Asn Leu Arg Glu Tyr Leu Gln Ala Arg Arg Pro
1               5                   10                  15

Pro
```

```
<210> SEQ ID NO 130
<211> LENGTH: 17
<212> TYPE: PRT
<213> ORGANISM: Unknown
<220> FEATURE:
<223> OTHER INFORMATION: Description of Unknown:
      FGFR2 peptide

<400> SEQUENCE: 130

Tyr Ala Ser Lys Gly Asn Leu Arg Glu Tyr Leu Arg Ala Arg Arg Pro
1               5                   10                  15

Pro

<210> SEQ ID NO 131
<211> LENGTH: 17
<212> TYPE: PRT
<213> ORGANISM: Unknown
<220> FEATURE:
<223> OTHER INFORMATION: Description of Unknown:
      FGFR3 peptide

<400> SEQUENCE: 131

Tyr Ala Ser Lys Gly Asn Leu Arg Glu Tyr Leu Arg Ala Arg Arg Pro
1               5                   10                  15

Pro

<210> SEQ ID NO 132
<211> LENGTH: 17
<212> TYPE: PRT
<213> ORGANISM: Unknown
<220> FEATURE:
<223> OTHER INFORMATION: Description of Unknown:
      FLT3 peptide

<400> SEQUENCE: 132

Tyr Cys Cys Tyr Gly Asp Leu Leu Asn Tyr Leu Arg Ser Lys Arg Glu
1               5                   10                  15

Lys

<210> SEQ ID NO 133
<211> LENGTH: 17
<212> TYPE: PRT
<213> ORGANISM: Unknown
<220> FEATURE:
<223> OTHER INFORMATION: Description of Unknown:
      PDGFRA peptide

<400> SEQUENCE: 133

Tyr Cys Phe Tyr Gly Asp Leu Val Asn Tyr Leu His Lys Asn Arg Asp
1               5                   10                  15

Ser

<210> SEQ ID NO 134
<211> LENGTH: 17
<212> TYPE: PRT
<213> ORGANISM: Unknown
<220> FEATURE:
<223> OTHER INFORMATION: Description of Unknown:
      ERBB3 peptide

<400> SEQUENCE: 134

Tyr Leu Pro Leu Gly Ser Leu Leu Asp His Val Arg Gln His Arg Gly
1               5                   10                  15
```

Ala

<210> SEQ ID NO 135
<211> LENGTH: 17
<212> TYPE: PRT
<213> ORGANISM: Unknown
<220> FEATURE:
<223> OTHER INFORMATION: Description of Unknown:
      ERBB4 peptide

<400> SEQUENCE: 135

Leu Met Pro His Gly Cys Leu Leu Glu Tyr Val His Glu His Lys Asp
1               5                   10                  15

Asn

<210> SEQ ID NO 136
<211> LENGTH: 17
<212> TYPE: PRT
<213> ORGANISM: Unknown
<220> FEATURE:
<223> OTHER INFORMATION: Description of Unknown:
      JAK2 peptide

<400> SEQUENCE: 136

Tyr Leu Pro Tyr Gly Ser Leu Arg Asp Tyr Leu Gln Lys His Lys Glu
1               5                   10                  15

Arg

<210> SEQ ID NO 137
<211> LENGTH: 17
<212> TYPE: PRT
<213> ORGANISM: Unknown
<220> FEATURE:
<223> OTHER INFORMATION: Description of Unknown:
      ROS1 peptide

<400> SEQUENCE: 137

Leu Met Glu Gly Gly Asp Leu Leu Thr Tyr Leu Arg Lys Ala Arg Met
1               5                   10                  15

Ala

<210> SEQ ID NO 138
<211> LENGTH: 22
<212> TYPE: DNA
<213> ORGANISM: Unknown
<220> FEATURE:
<223> OTHER INFORMATION: Description of Unknown:
      DDR2 oligonucleotide

<400> SEQUENCE: 138
gcatgaagta cctttcctct ct                                          22

<210> SEQ ID NO 139
<211> LENGTH: 22
<212> TYPE: DNA
<213> ORGANISM: Unknown
<220> FEATURE:
<223> OTHER INFORMATION: Description of Unknown:
      DDR2 oligonucleotide

<400> SEQUENCE: 139
gcatgaagta cytttcctct ct                                          22

<210> SEQ ID NO 140
<211> LENGTH: 22

```
<212> TYPE: DNA
<213> ORGANISM: Unknown
<220> FEATURE:
<223> OTHER INFORMATION: Description of Unknown:
      DDR2 oligonucleotide

<400> SEQUENCE: 140
gcatgaagta cttttcctct ct                                                 22

<210> SEQ ID NO 141
<211> LENGTH: 21
<212> TYPE: DNA
<213> ORGANISM: Unknown
<220> FEATURE:
<223> OTHER INFORMATION: Description of Unknown:
      DDR2 oligonucleotide

<400> SEQUENCE: 141
gcatgaagta ctttcctctc t                                                  21

<210> SEQ ID NO 142
<211> LENGTH: 20
<212> TYPE: DNA
<213> ORGANISM: Unknown
<220> FEATURE:
<223> OTHER INFORMATION: Description of Unknown:
      DDR2 oligonucleotide

<400> SEQUENCE: 142
gcatgaagta cctttcctct                                                    20

<210> SEQ ID NO 143
<211> LENGTH: 7
<212> TYPE: PRT
<213> ORGANISM: Unknown
<220> FEATURE:
<223> OTHER INFORMATION: Description of Unknown:
      DDR2 peptide

<400> SEQUENCE: 143

Gly Met Lys Tyr Leu Ser Ser
1               5

<210> SEQ ID NO 144
<211> LENGTH: 37
<212> TYPE: PRT
<213> ORGANISM: Unknown
<220> FEATURE:
<223> OTHER INFORMATION: Description of Unknown:
      DDR2 polypeptide

<400> SEQUENCE: 144

Val Ser Tyr Thr Asn Leu Lys Phe Met Ala Thr Gln Ile Ala Ser Gly
1               5                   10                  15

Met Lys Tyr Leu Ser Ser Leu Asn Phe Val His Arg Asp Leu Ala Thr
            20                  25                  30

Arg Asn Cys Leu Val
        35

<210> SEQ ID NO 145
<211> LENGTH: 37
<212> TYPE: PRT
<213> ORGANISM: Unknown
<220> FEATURE:
<223> OTHER INFORMATION: Description of Unknown:
      BRAF polypeptide
```

```
<400> SEQUENCE: 145

Phe Glu Met Ile Lys Leu Ile Asp Ile Ala Arg Gln Thr Ala Gln Gly
1               5                   10                  15

Met Asp Tyr Leu His Ala Lys Ser Ile Ile His Arg Asp Leu Lys Ser
            20                  25                  30

Asn Asn Ile Phe Leu
        35

<210> SEQ ID NO 146
<211> LENGTH: 37
<212> TYPE: PRT
<213> ORGANISM: Unknown
<220> FEATURE:
<223> OTHER INFORMATION: Description of Unknown:
      EGFR polypeptide

<400> SEQUENCE: 146

Ile Gly Ser Gln Tyr Leu Leu Asn Trp Cys Val Gln Ile Ala Lys Gly
1               5                   10                  15

Met Asn Tyr Leu Glu Asp Arg Arg Leu Val His Arg Asp Leu Ala Ala
            20                  25                  30

Arg Asn Val Leu Val
        35

<210> SEQ ID NO 147
<211> LENGTH: 37
<212> TYPE: PRT
<213> ORGANISM: Unknown
<220> FEATURE:
<223> OTHER INFORMATION: Description of Unknown:
      ERBB2 polypeptide

<400> SEQUENCE: 147

Leu Gly Ser Gln Asp Leu Leu Asn Trp Cys Met Gln Ile Ala Lys Gly
1               5                   10                  15

Met Ser Tyr Leu Glu Asp Val Arg Leu Val His Arg Asp Leu Ala Ala
            20                  25                  30

Arg Asn Val Leu Val
        35

<210> SEQ ID NO 148
<211> LENGTH: 37
<212> TYPE: PRT
<213> ORGANISM: Unknown
<220> FEATURE:
<223> OTHER INFORMATION: Description of Unknown:
      ABL1 polypeptide

<400> SEQUENCE: 148

Val Asn Ala Val Val Leu Leu Tyr Met Ala Thr Gln Ile Ser Ser Ala
1               5                   10                  15

Met Glu Tyr Leu Glu Lys Lys Asn Phe Ile His Arg Asp Leu Ala Ala
            20                  25                  30

Arg Asn Cys Leu Val
        35

<210> SEQ ID NO 149
<211> LENGTH: 37
<212> TYPE: PRT
<213> ORGANISM: Unknown
<220> FEATURE:
<223> OTHER INFORMATION: Description of Unknown:
      ALK polypeptide
```

<400> SEQUENCE: 149

Leu Ala Met Leu Asp Leu Leu His Val Ala Arg Asp Ile Ala Cys Gly
1               5                   10                  15

Cys Gln Tyr Leu Glu Glu Asn His Phe Ile His Arg Asp Ile Ala Ala
            20                  25                  30

Arg Asn Cys Leu Leu
            35

<210> SEQ ID NO 150
<211> LENGTH: 38
<212> TYPE: PRT
<213> ORGANISM: Unknown
<220> FEATURE:
<223> OTHER INFORMATION: Description of Unknown:
      AKT1 polypeptide

<400> SEQUENCE: 150

Phe Ser Glu Asp Arg Ala Arg Phe Tyr Gly Ala Glu Ile Val Ser Ala
1               5                   10                  15

Leu Asp Tyr Leu His Ser Glu Lys Asn Val Val Tyr Arg Asp Leu Lys
            20                  25                  30

Leu Glu Asn Leu Met Leu
            35

<210> SEQ ID NO 151
<211> LENGTH: 37
<212> TYPE: PRT
<213> ORGANISM: Unknown
<220> FEATURE:
<223> OTHER INFORMATION: Description of Unknown:
      MET polypeptide

<400> SEQUENCE: 151

Pro Thr Val Lys Asp Leu Ile Gly Phe Gly Leu Gln Val Ala Lys Gly
1               5                   10                  15

Met Lys Tyr Leu Ala Ser Lys Lys Phe Val His Arg Asp Leu Ala Ala
            20                  25                  30

Arg Asn Cys Met Leu
            35

<210> SEQ ID NO 152
<211> LENGTH: 37
<212> TYPE: PRT
<213> ORGANISM: Unknown
<220> FEATURE:
<223> OTHER INFORMATION: Description of Unknown:
      FGFR1 polypeptide

<400> SEQUENCE: 152

Leu Ser Ser Lys Asp Leu Val Ser Cys Ala Tyr Gln Val Ala Arg Gly
1               5                   10                  15

Met Glu Tyr Leu Ala Ser Lys Lys Cys Ile His Arg Asp Leu Ala Ala
            20                  25                  30

Arg Asn Val Leu Val
            35

<210> SEQ ID NO 153
<211> LENGTH: 37
<212> TYPE: PRT
<213> ORGANISM: Unknown
<220> FEATURE:
<223> OTHER INFORMATION: Description of Unknown:

FGFR2 polypeptide

<400> SEQUENCE: 153

Met Thr Phe Lys Asp Leu Val Ser Cys Thr Tyr Gln Val Ala Arg Gly
1               5                   10                  15

Met Glu Tyr Leu Ala Ser Gln Lys Cys Ile His Arg Asp Leu Ala Ala
            20                  25                  30

Arg Asn Val Leu Val
        35

<210> SEQ ID NO 154
<211> LENGTH: 37
<212> TYPE: PRT
<213> ORGANISM: Unknown
<220> FEATURE:
<223> OTHER INFORMATION: Description of Unknown:
      FGFR3 polypeptide

<400> SEQUENCE: 154

Leu Thr Phe Lys Asp Leu Val Ser Cys Ala Tyr Gln Val Ala Arg Gly
1               5                   10                  15

Met Glu Tyr Leu Ala Ser Gln Lys Cys Ile His Arg Asp Leu Ala Ala
            20                  25                  30

Arg Asn Val Leu Val
        35

<210> SEQ ID NO 155
<211> LENGTH: 37
<212> TYPE: PRT
<213> ORGANISM: Unknown
<220> FEATURE:
<223> OTHER INFORMATION: Description of Unknown:
      FLT3 polypeptide

<400> SEQUENCE: 155

Leu Thr Phe Glu Asp Leu Leu Cys Phe Ala Tyr Gln Val Ala Lys Gly
1               5                   10                  15

Met Glu Phe Leu Glu Phe Lys Ser Cys Val His Arg Asp Leu Ala Ala
            20                  25                  30

Arg Asn Val Leu Val
        35

<210> SEQ ID NO 156
<211> LENGTH: 37
<212> TYPE: PRT
<213> ORGANISM: Unknown
<220> FEATURE:
<223> OTHER INFORMATION: Description of Unknown:
      PDGFRA polypeptide

<400> SEQUENCE: 156

Leu Thr Leu Leu Asp Leu Leu Ser Phe Thr Tyr Gln Val Ala Arg Gly
1               5                   10                  15

Met Glu Phe Leu Ala Ser Lys Asn Cys Val His Arg Asp Leu Ala Ala
            20                  25                  30

Arg Asn Val Leu Leu
        35

<210> SEQ ID NO 157
<211> LENGTH: 37
<212> TYPE: PRT
<213> ORGANISM: Unknown
<220> FEATURE:

```
<223> OTHER INFORMATION: Description of Unknown:
      ERBB3 polypeptide

<400> SEQUENCE: 157

Leu Gly Pro Gln Leu Leu Leu Asn Trp Gly Val Gln Ile Ala Lys Gly
1               5                   10                  15

Met Tyr Tyr Leu Glu Glu His Gly Met Val His Arg Asn Leu Ala Ala
            20                  25                  30

Arg Asn Val Leu Leu
        35

<210> SEQ ID NO 158
<211> LENGTH: 37
<212> TYPE: PRT
<213> ORGANISM: Unknown
<220> FEATURE:
<223> OTHER INFORMATION: Description of Unknown:
      ERBB4 polypeptide

<400> SEQUENCE: 158

Ile Gly Ser Gln Leu Leu Leu Asn Trp Cys Val Gln Ile Ala Lys Gly
1               5                   10                  15

Met Met Tyr Leu Glu Glu Arg Arg Leu Val His Arg Asp Leu Ala Ala
            20                  25                  30

Arg Asn Val Leu Val
        35

<210> SEQ ID NO 159
<211> LENGTH: 37
<212> TYPE: PRT
<213> ORGANISM: Unknown
<220> FEATURE:
<223> OTHER INFORMATION: Description of Unknown:
      JAK2 polypeptide

<400> SEQUENCE: 159

Ile Asp His Ile Lys Leu Leu Gln Tyr Thr Ser Gln Ile Cys Lys Gly
1               5                   10                  15

Met Glu Tyr Leu Gly Thr Lys Arg Tyr Ile His Arg Asp Leu Ala Thr
            20                  25                  30

Arg Asn Ile Leu Val
        35

<210> SEQ ID NO 160
<211> LENGTH: 37
<212> TYPE: PRT
<213> ORGANISM: Unknown
<220> FEATURE:
<223> OTHER INFORMATION: Description of Unknown:
      ROS1 polypeptide

<400> SEQUENCE: 160

Leu Thr Leu Val Asp Leu Val Asp Leu Cys Val Asp Ile Ser Lys Gly
1               5                   10                  15

Cys Val Tyr Leu Glu Arg Met His Phe Ile His Arg Asp Leu Ala Ala
            20                  25                  30

Arg Asn Cys Leu Val
        35

<210> SEQ ID NO 161
<211> LENGTH: 84
<212> TYPE: DNA
<213> ORGANISM: Unknown
```

<220> FEATURE:
<223> OTHER INFORMATION: Description of Unknown:
      DDR2 oligonucleotide

<400> SEQUENCE: 161
acaccaatct gaagtttatg ctacccaaa ttgcctctgg catgaagtac ctttyctctc    60
ttaattttgt tcaccgagat ctgg                                          84

<210> SEQ ID NO 162
<211> LENGTH: 84
<212> TYPE: DNA
<213> ORGANISM: Unknown
<220> FEATURE:
<223> OTHER INFORMATION: Description of Unknown:
      DDR2 oligonucleotide

<400> SEQUENCE: 162
acaccaatct gaagtttatg ctacccaaa ttgcctctgg catgaagtac ctttcctctc    60
ttaattttgt tcaccgagat ctgg                                          84

<210> SEQ ID NO 163
<211> LENGTH: 28
<212> TYPE: PRT
<213> ORGANISM: Unknown
<220> FEATURE:
<223> OTHER INFORMATION: Description of Unknown:
      DDR2 peptide

<400> SEQUENCE: 163

Tyr Thr Asn Leu Lys Phe Met Ala Thr Gln Ile Ala Ser Gly Met Lys
1               5                   10                  15

Tyr Leu Ser Ser Leu Asn Phe Val His Arg Asp Leu
            20                  25

<210> SEQ ID NO 164
<211> LENGTH: 81
<212> TYPE: DNA
<213> ORGANISM: Unknown
<220> FEATURE:
<223> OTHER INFORMATION: Description of Unknown:
      DDR2 oligonucleotide

<400> SEQUENCE: 164
gtgctggatg gaaatagtaa mccctatgac attttcctaa aggacttgga gccgcccatt    60
gtagccagat ttgtccggtt c                                              81

<210> SEQ ID NO 165
<211> LENGTH: 81
<212> TYPE: DNA
<213> ORGANISM: Unknown
<220> FEATURE:
<223> OTHER INFORMATION: Description of Unknown:
      DDR2 oligonucleotide

<400> SEQUENCE: 165
gtgctggatg gaaatagtaa cccctatgac attttcctaa aggacttgga gccgcccatt    60
gtagccagat ttgtccggtt c                                              81

<210> SEQ ID NO 166
<211> LENGTH: 27
<212> TYPE: PRT
<213> ORGANISM: Unknown
<220> FEATURE:
<223> OTHER INFORMATION: Description of Unknown:

DDR2 peptide

<400> SEQUENCE: 166

Val Leu Asp Gly Asn Ser Asn Pro Tyr Asp Ile Phe Leu Lys Asp Leu
1               5                   10                  15

Glu Pro Pro Ile Val Ala Arg Phe Val Arg Phe
            20                  25

<210> SEQ ID NO 167
<211> LENGTH: 81
<212> TYPE: DNA
<213> ORGANISM: Unknown
<220> FEATURE:
<223> OTHER INFORMATION: Description of Unknown:
      DDR2 oligonucleotide

<400> SEQUENCE: 167
gatccaatgc ttaaagttga tgacagcaac actcrgatcc tgattggctg cttggtggcc    60
atcatcttta tcctcctggc c                                              81

<210> SEQ ID NO 168
<211> LENGTH: 81
<212> TYPE: DNA
<213> ORGANISM: Unknown
<220> FEATURE:
<223> OTHER INFORMATION: Description of Unknown:
      DDR2 oligonucleotide

<400> SEQUENCE: 168
gatccaatgc ttaaagttga tgacagcaac actcggatcc tgattggctg cttggtggcc    60
atcatcttta tcctcctggc c                                              81

<210> SEQ ID NO 169
<211> LENGTH: 27
<212> TYPE: PRT
<213> ORGANISM: Unknown
<220> FEATURE:
<223> OTHER INFORMATION: Description of Unknown:
      DDR2 peptide

<400> SEQUENCE: 169

Asp Pro Met Leu Lys Val Asp Asp Ser Asn Thr Arg Ile Leu Ile Gly
1               5                   10                  15

Cys Leu Val Ala Ile Ile Phe Ile Leu Leu Ala
            20                  25

<210> SEQ ID NO 170
<211> LENGTH: 855
<212> TYPE: PRT
<213> ORGANISM: Homo sapiens

<400> SEQUENCE: 170

Met Ile Leu Ile Pro Arg Met Leu Leu Val Leu Phe Leu Leu Leu Pro
1               5                   10                  15

Ile Leu Ser Ser Ala Lys Ala Gln Val Asn Pro Ala Ile Cys Arg Tyr
            20                  25                  30

Pro Leu Gly Met Ser Gly Gly Gln Ile Pro Asp Glu Asp Ile Thr Ala
        35                  40                  45

Ser Ser Gln Trp Ser Glu Ser Thr Ala Ala Lys Tyr Gly Arg Leu Asp
    50                  55                  60

Ser Glu Glu Gly Asp Gly Ala Trp Cys Pro Ile Pro Val Glu Pro
65                  70                  75                  80

```
Asp Asp Leu Lys Glu Phe Leu Gln Ile Asp Leu His Thr Leu His Phe
            85                  90                  95

Ile Thr Leu Val Gly Thr Gln Gly Arg His Ala Gly Gly His Gly Ile
            100                 105                 110

Glu Phe Ala Pro Met Tyr Lys Ile Asn Tyr Ser Arg Asp Gly Thr Arg
            115                 120                 125

Trp Ile Ser Trp Arg Asn Arg His Gly Lys Gln Val Leu Asp Gly Asn
            130                 135                 140

Ser Asn Pro Tyr Asp Ile Phe Leu Lys Asp Leu Glu Pro Pro Ile Val
145                 150                 155                 160

Ala Arg Phe Val Arg Phe Ile Pro Val Thr Asp His Ser Met Asn Val
            165                 170                 175

Cys Met Arg Val Glu Leu Tyr Gly Cys Val Trp Leu Asp Gly Leu Val
            180                 185                 190

Ser Tyr Asn Ala Pro Ala Gly Gln Gln Phe Val Leu Pro Gly Gly Ser
            195                 200                 205

Ile Ile Tyr Leu Asn Asp Ser Val Tyr Asp Gly Ala Val Gly Tyr Ser
            210                 215                 220

Met Thr Glu Gly Leu Gly Gln Leu Thr Asp Gly Val Ser Gly Leu Asp
225                 230                 235                 240

Asp Phe Thr Gln Thr His Glu Tyr His Val Trp Pro Gly Tyr Asp Tyr
            245                 250                 255

Val Gly Trp Arg Asn Glu Ser Ala Thr Asn Gly Tyr Ile Glu Ile Met
            260                 265                 270

Phe Glu Phe Asp Arg Ile Arg Asn Phe Thr Thr Met Lys Val His Cys
            275                 280                 285

Asn Asn Met Phe Ala Lys Gly Val Lys Ile Phe Lys Glu Val Gln Cys
            290                 295                 300

Tyr Phe Arg Ser Glu Ala Ser Glu Trp Glu Pro Asn Ala Ile Ser Phe
305                 310                 315                 320

Pro Leu Val Leu Asp Asp Val Asn Pro Ser Ala Arg Phe Val Thr Val
            325                 330                 335

Pro Leu His His Arg Met Ala Ser Ala Ile Lys Cys Gln Tyr His Phe
            340                 345                 350

Ala Asp Thr Trp Met Met Phe Ser Glu Ile Thr Phe Gln Ser Asp Ala
            355                 360                 365

Ala Met Tyr Asn Asn Ser Glu Ala Leu Pro Thr Ser Pro Met Ala Pro
            370                 375                 380

Thr Thr Tyr Asp Pro Met Leu Lys Val Asp Asp Ser Asn Thr Arg Ile
385                 390                 395                 400

Leu Ile Gly Cys Leu Val Ala Ile Ile Phe Ile Leu Leu Ala Ile Ile
            405                 410                 415

Val Ile Ile Leu Trp Arg Gln Phe Trp Gln Lys Met Leu Glu Lys Ala
            420                 425                 430

Ser Arg Arg Met Leu Asp Asp Glu Met Thr Val Ser Leu Ser Leu Pro
            435                 440                 445

Ser Asp Ser Ser Met Phe Asn Asn Asn Arg Ser Ser Ser Pro Ser Glu
450                 455                 460

Gln Gly Ser Asn Ser Thr Tyr Asp Arg Ile Phe Pro Leu Arg Pro Asp
465                 470                 475                 480

Tyr Gln Glu Pro Ser Arg Leu Ile Arg Lys Leu Pro Glu Phe Ala Pro
            485                 490                 495
```

```
Gly Glu Glu Glu Ser Gly Cys Ser Gly Val Val Lys Pro Val Gln Pro
            500                 505                 510

Ser Gly Pro Glu Gly Val Pro His Tyr Ala Glu Ala Asp Ile Val Asn
        515                 520                 525

Leu Gln Gly Val Thr Gly Gly Asn Thr Tyr Ser Val Pro Ala Val Thr
    530                 535                 540

Met Asp Leu Leu Ser Gly Lys Asp Val Ala Val Glu Glu Phe Pro Arg
545                 550                 555                 560

Lys Leu Leu Thr Phe Lys Glu Lys Leu Glu Gly Gln Phe Gly Glu
                565                 570                 575

Val His Leu Cys Glu Val Glu Gly Met Glu Lys Phe Lys Asp Lys Asp
            580                 585                 590

Phe Ala Leu Asp Val Ser Ala Asn Gln Pro Val Leu Val Ala Val Lys
                595                 600                 605

Met Leu Arg Ala Asp Ala Asn Lys Asn Ala Arg Asn Asp Phe Leu Lys
            610                 615                 620

Glu Ile Lys Ile Met Ser Arg Leu Lys Asp Pro Asn Ile Ile His Leu
625                 630                 635                 640

Leu Ala Val Cys Ile Thr Asp Asp Pro Leu Cys Met Ile Thr Glu Tyr
                645                 650                 655

Met Glu Asn Gly Asp Leu Asn Gln Phe Leu Ser Arg His Glu Pro Pro
                660                 665                 670

Asn Ser Ser Ser Asp Val Arg Thr Val Ser Tyr Thr Asn Leu Lys
            675                 680                 685

Phe Met Ala Thr Gln Ile Ala Ser Gly Met Lys Tyr Leu Ser Ser Leu
            690                 695                 700

Asn Phe Val His Arg Asp Leu Ala Thr Arg Asn Cys Leu Val Gly Lys
705                 710                 715                 720

Asn Tyr Thr Ile Lys Ile Ala Asp Phe Gly Met Ser Arg Asn Leu Tyr
                725                 730                 735

Ser Gly Asp Tyr Tyr Arg Ile Gln Gly Arg Ala Val Leu Pro Ile Arg
            740                 745                 750

Trp Met Ser Trp Glu Ser Ile Leu Leu Gly Lys Phe Thr Thr Ala Ser
            755                 760                 765

Asp Val Trp Ala Phe Gly Val Thr Leu Trp Glu Thr Phe Thr Phe Cys
            770                 775                 780

Gln Glu Gln Pro Tyr Ser Gln Leu Ser Asp Glu Gln Val Ile Glu Asn
785                 790                 795                 800

Thr Gly Glu Phe Phe Arg Asp Gln Gly Arg Gln Thr Tyr Leu Pro Gln
                805                 810                 815

Pro Ala Ile Cys Pro Asp Ser Val Tyr Lys Leu Met Leu Ser Cys Trp
            820                 825                 830

Arg Arg Asp Thr Lys Asn Arg Pro Ser Phe Gln Glu Ile His Leu Leu
            835                 840                 845

Leu Leu Gln Gln Gly Asp Glu
850                 855
```